United States Patent
Obenchain (12)

(10) Patent No.: US 8,653,979 B2
(45) Date of Patent: Feb. 18, 2014

(54) GAS FLOW AND PRESSURE ERROR ALARM

(76) Inventor: Valerie A. Obenchain, Newaygo, MI (US)

( * ) Notice: Subject to any disclaimer, the term of this patent is extended or adjusted under 35 U.S.C. 154(b) by 213 days.

(21) Appl. No.: 13/085,877

(22) Filed: Apr. 13, 2011

(65) Prior Publication Data

US 2011/0248856 A1   Oct. 13, 2011

Related U.S. Application Data

(60) Provisional application No. 61/323,845, filed on Apr. 13, 2010.

(51) Int. Cl.
*G08B 21/00* (2006.01)
*F16K 37/00* (2006.01)

(52) U.S. Cl.
USPC ............ 340/606; 137/557; 340/623; 700/282

(58) Field of Classification Search
USPC ................. 73/40.5, 861; 128/202.22, 204.19, 128/204.22, 204.24, 205.24; 137/2, 8, 12, 137/14, 488, 552, 557; 261/38; 340/603, 340/605, 606, 612, 623, 626; 454/238, 239, 454/251, 255, 256, 340, 341; 600/323; 700/282, 301; 702/45, 47, 50, 116; 709/606
See application file for complete search history.

(56) References Cited

U.S. PATENT DOCUMENTS

| | | | |
|---|---|---|---|
| 3,740,739 A * | 6/1973 | Griffin et al. | 367/83 |
| 3,823,575 A * | 7/1974 | Parel | 62/51.2 |
| 4,763,114 A * | 8/1988 | Eidsmore | 340/606 |
| 5,554,976 A * | 9/1996 | Miyauchi et al. | 340/626 |
| 5,788,688 A * | 8/1998 | Bauer et al. | 606/1 |
| 6,575,164 B1 * | 6/2003 | Jaffe et al. | 128/205.24 |
| 6,683,535 B1 * | 1/2004 | Utke | 340/604 |
| 2002/0088464 A1 * | 7/2002 | Truschel | 128/204.18 |
| 2002/0195105 A1 * | 12/2002 | Blue et al. | 128/204.21 |
| 2004/0159323 A1 * | 8/2004 | Schmidt et al. | 128/204.23 |
| 2004/0204870 A1 * | 10/2004 | Schimnowski et al. | 702/45 |
| 2004/0217871 A1 * | 11/2004 | Shoub | 340/606 |
| 2005/0024216 A1 * | 2/2005 | Crooks et al. | 340/606 |
| 2005/0083205 A1 * | 4/2005 | Deacy | 340/628 |
| 2006/0219245 A1 * | 10/2006 | Holder | 128/204.26 |
| 2006/0290525 A1 * | 12/2006 | Andersen et al. | 340/632 |
| 2007/0193340 A1 * | 8/2007 | Yoshida | 73/46 |
| 2008/0072904 A1 * | 3/2008 | Becker et al. | 128/204.22 |
| 2011/0213531 A1 * | 9/2011 | Farley et al. | 701/50 |

FOREIGN PATENT DOCUMENTS

JP  05044899 A  *  2/1993  ............ F17D 1/02

* cited by examiner

*Primary Examiner* — Steven Lim
*Assistant Examiner* — Stephen Burgdorf
(74) *Attorney, Agent, or Firm* — Kohn & Associates, PLLC

(57) ABSTRACT

A gas flow warning alarm device to produce an alarm indication when the gas flow rate in a pressurized gas system violates at least one predetermined limit. The alarm device includes a gas flow sensing and error signaling subassembly to generate an error signal upon sensing a violative gas flow rate, and an indicator subassembly activatable by an error signal to produce an alarm indication. The gas flow warning alarm device responds both to the depletion of a pressurized gas reservoir and to blockages and disconnections in a gas line downstream of a regulator. A method for detecting gas flow malfunctions in a pressurized gas system. A reservoir changing device to open a filled reserve reservoir of gas to a pressurized gas system upon receiving an alarm indication that pressure in a primary gas reservoir has fallen below a predetermined limit.

43 Claims, 19 Drawing Sheets

GAS FLOW AND PRESSURE ERROR ALARM

TECHNICAL FIELD

The present invention relates generally to an alarm device to warn of malfunctions in a pressurized gas system and more specifically to an alarm device to warn of gas flow and gas pressure malfunctions in a medical gas system.

BACKGROUND OF THE INVENTION

Pressurized gas systems are used in respiratory therapy, in medical procedures and testing, in the breathing apparatuses of divers and firefighters, and in such industrial fields as welding, heating, ventilation, and air conditioning (HVAC), and plumbing. It is important to provide users of these systems with an alarm to indicate that the supply of gas has been or is about to be exhausted, or that the flow of gas has been interrupted. Pressurized gas alarm systems indicate these conditions by means of audible alarms, alarm lights, and the like. Such alarms are especially critical in medical gas uses, where a patient's life may be threatened by the interruption of the flow of oxygen or other gas. In a medical setting, a warning alarm must be perceived not only by the end user of the gas, who may be an incapacitated patient, but also by caregivers, who may be at sites remote from the end user. It is therefore desirable to provide electrically powered alarms, whose warnings can be communicated over distances by wires or by wireless broadcast systems.

A typical pressurized gas system includes a cylinder, tank, canister, or other reservoir, to store a gas at high pressure, and a regulator to allow the gas to flow into a gas line at a constant reduced pressure, and at an appropriate flow rate. The term "pressurized gas system" is defined to include a cylinder or other pressurized reservoir, the regulator, all lines which conduct the gas, and the end use appliance such as a mask, cannula, tent, incubator, or torch. The term "downstream" is defined as the direction of gas flow away from a cylinder or other reservoir. Typically, a gas cylinder includes a main valve and cylinder connector to which a regulator is attached. When the cylinder valve is opened, pressurized gas is admitted into the regulator. Regulators typically include at least two valves. A pressure valve maintains a constant user selected pressure downstream of the cylinder. It maintains that pressure as tank pressure decreases and downstream demand changes, typically by means of a diaphragm-controlled valve. A flow valve, downstream of the pressure valve, regulates the flow rate of gas out of the regulator. It is the flow valve that directly determines the flow rate of gas into a downstream appliance.

There are two types of malfunction that can cause a loss of gas flow at a downstream appliance. The first cause is the exhaustion of gas in the cylinder. Cylinder pressure alarm devices exist in the prior art to provide an alarm indication when a gas cylinder has been exhausted, or when gas pressure in the cylinder has fallen to a predetermined limit. These alarm devices generally include a cylinder pressure sensor that actuates an electronic or mechanical alarm when cylinder pressure reaches a minimum set point. These devices sense gas pressure at a point downstream of the cylinder valve and upstream of the pressure valve of the regulator. It is in this region that tank pressure can be reliably sensed when the cylinder valve is open. Such devices are disclosed in U.S. Pat. No. 6,209,579 to Bowden et al, U.S. Pat. No. 5,040,477 to Schiffmacher, U.S. Pat. No. 6,137,417 to McDermott, and U.S. Patent Application Publication No. US2010/0097232 to Lee et al.

A cylinder pressure sensor, however, is ineffective at detecting the second type of gas flow malfunction: malfunctions that occur in the gas lines downstream of the flow valve of a flow regulator. These downstream malfunctions include the disconnection of a gas line from the flow valve; the disconnection of two joined gas lines; the disconnection of a gas line from an appliance; a leak in a gas line or appliance; and blockages, such as a clog or kink in a gas line.

Cylinder pressure alarms cannot react to these downstream malfunctions. Their pressure sensors are isolated from pressure and flow conditions in the downstream gas lines by at least the pressure valve and flow valve, and in some cases by additional intervening valves. Cylinder pressure alarms are also inapplicable to oxygen concentrators.

Alarm devices which monitor gas flow rate have the potential to detect malfunctions occurring downstream of a regulator, and also to detect depletion of a pressurized gas cylinder or other reservoir. They are also potentially applicable to oxygen concentrators and other devices that employ fans or compressors to generate a gas flow. Disconnections, leaks and blockages, are detectable by gas flow detectors as reductions in gas flow rate by a gas flow sensor located downstream of the malfunction. Disconnections and leaks can also be detected by gas flow sensors upstream of the malfunction, as increases in gas flow rate, which reflect the decreased gas flow resistance caused by a disconnection or leak. The depletion of a gas cylinder or other gas reservoir is also detectable by a gas flow detector situated downstream of a regulator. Even though a regulator buffers the downstream gas lines from changes in cylinder pressure, the near or complete exhaustion of the cylinder will of course produce detectable reduction in gas flow rate downstream. Alarm devices which monitor gas flow are also applicable to oxygen concentrators and other devices that produce gas flow by means of fans or compressors, rather than by means of a pressurized cylinder.

A gas flow alarm device exists in the prior art, but it cannot warn of all malfunctions occurring downstream of a regulator, or of the depletion of a pressurized gas cylinder or other reservoir. U.S. Pat. No. 6,386,196 to Culton discloses a gas flow alarm to detect the detachment of an oxygen line from an oxygen cannula, or between two segments of oxygen line. The alarm consists of a coupler with a proximal end accepting an upstream oxygen line and a distal end connecting to a downstream oxygen line or cannula. The coupler includes an audible alarm, in the form of a whistle at the proximal end. The whistle is normally occluded by the downstream line but is uncovered when the line is disconnected. Upon disconnection, the uncovered whistle, powered by the gas flow from upstream, emits an audible alarm tone. The coupler also includes a visual indication of flow, a small propeller, enclosed in the coupler, which rotates in the gas flow.

The alarm device disclosed by Culton can only sound an alarm in response to a disconnection downstream of the alarm device itself. It cannot sound an alarm if there is a disconnection, leak, or blockage upstream of the alarm device, or if the gas reservoir becomes exhausted. These malfunctions all cut off the gas flow which powers the whistle. The duration of the whistle alert is also limited by the amount of gas available to power the whistle. Furthermore, the whistle can only be perceived by those in the immediate vicinity of the alarm. Should a gas flow malfunction occur upstream of the alarm disclosed by Culton, the only warning is the cessation of rotation of the small enclosed propeller. This cessation is perceivable only by individuals who happen to be scrutinizing the propeller at the time of malfunction. This hardly qualifies as a warning.

There is a need for a gas flow warning alarm that can detect the gas flow malfunctions at any point downstream of a regulator, detects cylinder exhaustion, and produces an alarm indication that is autonomous of gas pressure and perceivable at remote locations and without constant scrutiny of the alarm device. A warning alarm device that detects gas flow malfunctions downstream of a regulator flow valve has one shortcoming. It can provide little advance warning of exhaustion of a gas cylinder or other pressurized gas reservoir. Because a regulator maintains constant flow, exhaustion of the cylinder can be detected only at the point where cylinder pressure has fallen to the point where gas flow ceases. A device that senses cylinder pressure upstream of a regulator pressure valve can be set to provide an alarm at a predetermined pressure, which can be set high enough to provide advance warning of depletion.

When cylinder pressure does drop below a predetermined limit, there may be no one available to perceive an alarm indication or to exchange a depleted cylinder for a fresh cylinder. There is therefore a need for a device that changes the source of a pressurized gas system from a primary reservoir to a reserve reservoir, in response to an alarm indication.

SUMMARY OF THE INVENTION

The present invention provides a gas flow warning alarm device to produce an alarm indication when the gas flow rate in a pressurized gas system violates at least one predetermined limit. The alarm device includes a flow sensing and error signal generating subassembly including a gas flow sensor to sense a gas flow rate, and an error signal generator operatively connected to the gas flow sensor. The gas flow sensor is configured to actuate the error signal generator upon detecting a gas flow rate that violates the predetermined limit. The error signal generator is configured to generate an error signal in response to actuation by the flow rate sensor. The alarm device further includes an indicator subassembly including at least one indicator mechanism operatively connected to the error signal generator. The indicator mechanism is activatable by an error signal to produce perceptible alarm indications, including visible, audible, and broadcast alarms. The warning alarm device further includes at least one power subassembly including at least one power source operatively connected to a master power switch to provide power to the flow sensing and error signal generating subassembly and indicator subassembly, and to permit a user to activate and deactivate the alarm device.

The present invention also provides a fluid flow warning alarm device for producing an alarm indication when the fluid flow rate in a pressurized fluid system violates at least one predetermined limit.

The present invention further provides a method for detecting gas flow malfunctions in a pressurized gas system, including the steps of engaging a gas flow inlet of a flow sensor to a pressurized gas system downstream of a gas regulator, engaging a gas flow outlet of a flow sensor to the pressurized gas system downstream of the gas flow outlet and upstream of an end use appliance, sensing a gas flow rate violating at least one predetermined limit, actuating a gas flow error signal generator, generating a gas flow error signal, activating an indicator mechanism by means of the gas flow error signal, and producing a perceptible gas flow alarm indication by means of the indicator mechanism.

The present invention also provides a reservoir changing device to open a filled reserve reservoir of gas to a pressurized gas system upon receiving an alarm indication that pressure in a primary gas reservoir has fallen below a predetermined limit.

BRIEF DESCRIPTION OF THE DRAWINGS

Other advantages of the present invention will be readily appreciated as the same becomes better understood by reference to the following detailed description when considered in connection with the accompanying drawings, which are not necessarily drawn to scale, wherein.

DETAILED DESCRIPTION OF THE INVENTION

Figure 1:
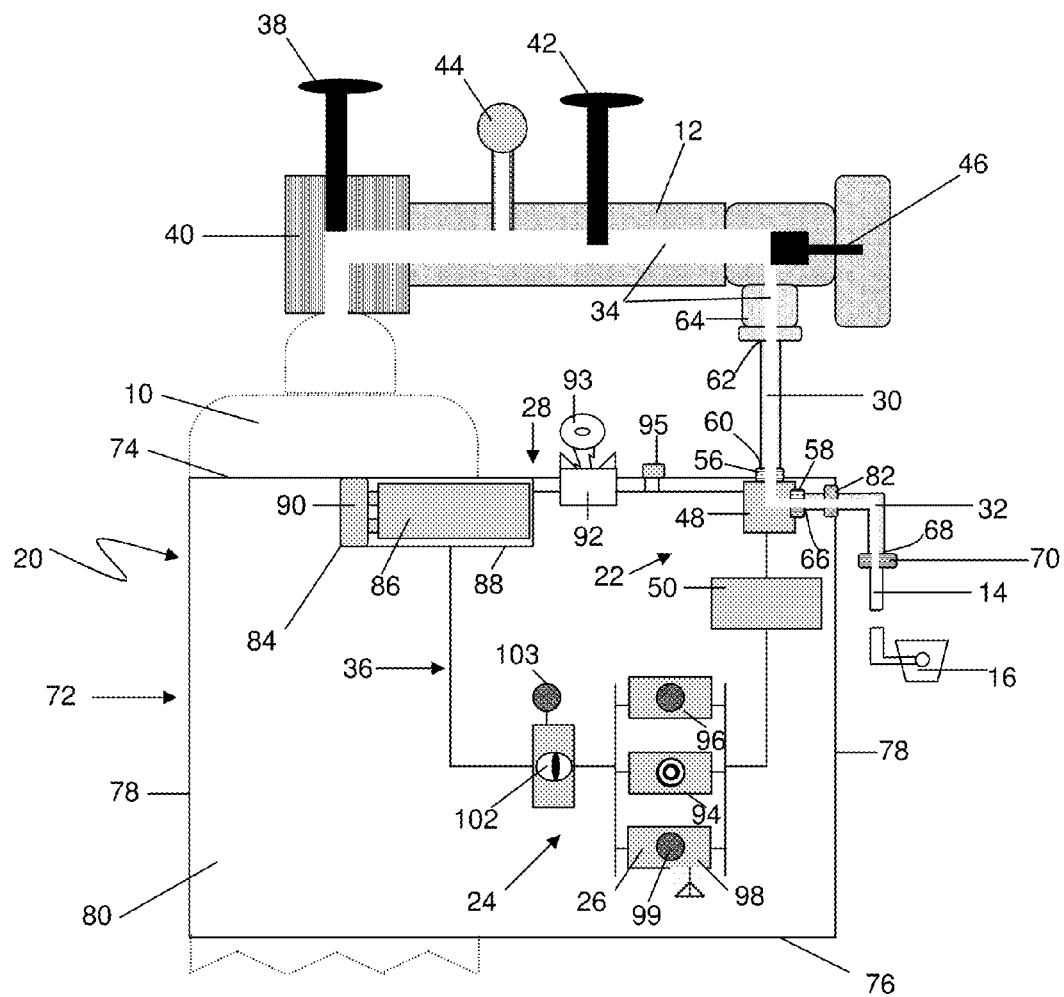
FIG. 1 shows a frontal semi-schematic view of the alarm device of the present invention, with front wall of housing removed.

A pressurized gas system is defined as a continuous series of vessels in gas-tight interrelationship for conducting gas from a region of high pressure to a region of low pressure. In the example illustrated in FIG. 1, the pressurized gas system is taken to include a gas cylinder 10 or other reservoir, a regulator 12, and all gas lines 14 and appliances 16 downstream of the regulator 12, exclusive of those incorporated into the present invention, which is generally shown at 20.

The alarm device 20 includes a flow sensing and error signaling subassembly 22 to sense a gas flow rate in the pressurized gas system and to generate an error signal when the gas flow rate violates at least one predetermined limit. Preferably the flow sensing and error signaling subassembly 22 is configured to generate an error signal when the gas flow rate violates either an upper or a lower limit. This permits detection of such malfunctions as obstructions or kinks in the pressurized gas system, or of depletion of the cylinder 10, both of which decrease gas flow rates downstream of the malfunction. The sensing of both upper and lower limit violations also permits the detection of leaks or disconnections in the pressurized gas system upstream of the leak or disconnection, because these malfunctions decrease resistance to gas flow, thereby increasing flow rate as detected upstream. Less preferably, the flow sensing and error signaling subassembly 22 can be configured to generate an error signal when the gas flow rate violates either a lower or an upper limit.

The alarm device 20 also includes an indicator subassembly 24, including at least one indicator mechanism 26 operatively connected to the flow sensing and error signaling subassembly 22 to produce a perceptible alarm indication in response to an error signal; a power subassembly 28 to provide and control electrical power to the flow sensing and error signaling subassembly 22 and indicator subassembly 24; and, optionally, tubular gas flow inlet and outlet conduits, 30 and 32 respectively, to direct a column of pressurized gas 34 into the flow sensing and error signaling subassembly 22. The alarm device also includes connection means 36 such as wiring, printed circuits, and the like, as required to operatively interconnect the components of the flow sensing and error signaling subassembly 22, indicator subassembly 24, and power subassembly 28.

Figure 2:
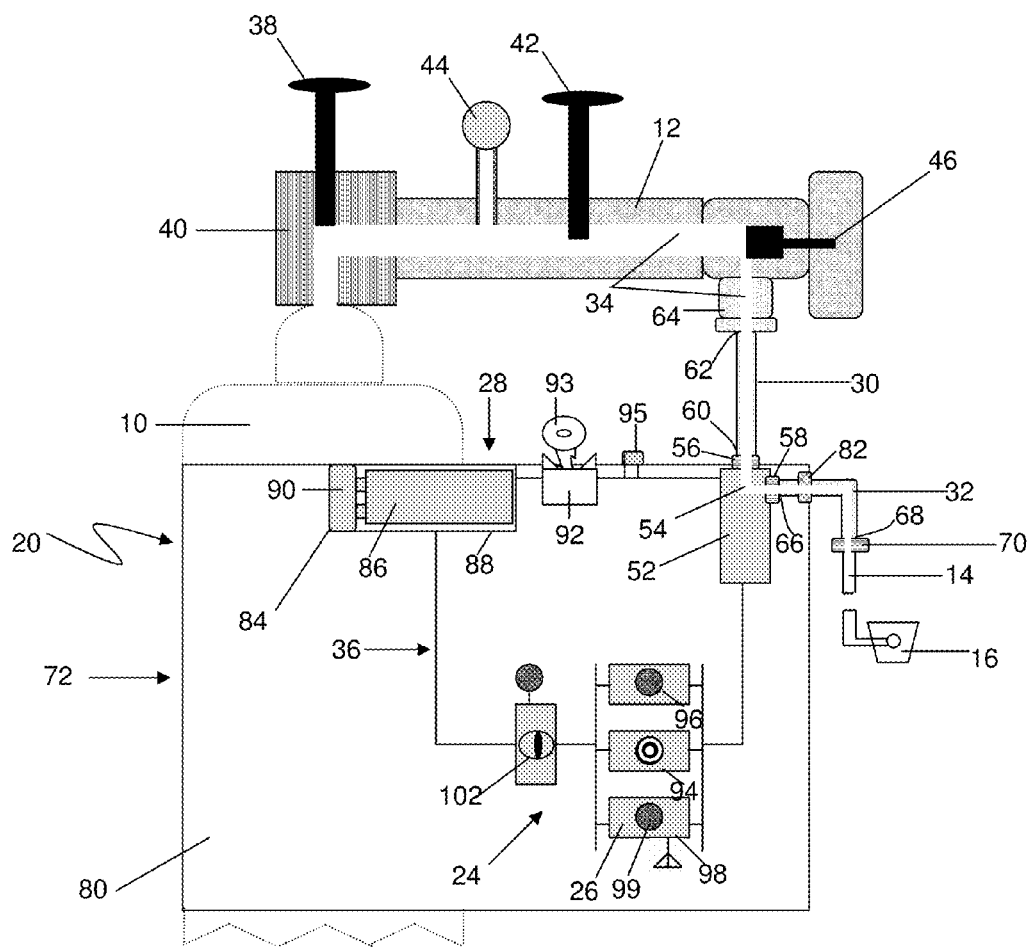
FIG. 2 shows a frontal semi-schematic view of the alarm device wherein the gas flow sensor and error signal generator are incorporated into a flow switch.

An example of the device of the present invention, adapted for use with a typical pressurized gas tank and regulator system for gases, is illustrated in FIG. 2. Oxygen is stored under pressure in the cylinder 10. The cylinder 10 includes a main valve 38 and a cylinder connector 40 to which the regulator 12 is attached in gas-tight engagement. The main valve 38 is opened to admit pressurized gas into the regulator 12. The regulator 12 includes a pressure valve 42 to regulate the pressure of gas exerted downstream of the cylinder 10. With the main valve 38 fully opened, cylinder pressure can be sensed reliably in the region downstream of the main valve 38 and upstream of the pressure valve 42. A cylinder pressure gauge 44 is often interposed into the pressurized gas stream 34 in this region. The regulator 12 also includes a flow valve 46, downstream of the pressure valve 42, to regulate the flow rate of gas downstream of the regulator 12. It is the flow valve 46 that determines the flow rate of gas into a downstream appliance 16, such as an oxygen mask or oxygen cannula. Gas flow rate can be sensed in the region downstream of the flow valve 46 and upstream of the appliance 16. It is the gas flow in this region that is sensed by the alarm device of the present invention.

The gas flow sensing and error signaling subassembly 22 includes a gas flow sensor 48 and an error signal generator 50. The gas flow sensor 48, upon detecting a gas flow rate violating a predetermined limit, is configured to induce the error signal generator to generate an error signal, preferably in the form of an electrical current.

Preferably gas flow sensor 48 and the error signal generator 50 are incorporated into a single unit, a gas flow switch 52, as illustrated in FIG. 2. The gas flow switch 52 includes an internal cavity 54 containing a sensor mechanism (not shown) and communicating with the pressurized gas system through a gas flow inlet 56 and a gas flow outlet 58. The gas flow inlet 56 receives the pressurized gas column 34, or a portion of thereof, via the gas flow inlet conduit 30. The gas flow inlet conduit 30 includes a downstream orifice 60 in gas-tight engagement with the gas flow inlet 56 of the gas flow switch 52, and an upstream orifice 62 in gas-tight engagement with the pressurized gas system at any point downstream of the flow valve 46 and upstream of the end use appliance 16. In the example illustrated in FIG. 2, the upstream orifice 62 of the gas flow inlet conduit 30 is mounted in gas-tight engagement with a regulator outlet 64 attached to the flow valve 46 of the regulator 12. Alternatively, the upstream orifice 62 can be engaged with the gas line 14 or appliance 16 at any point downstream of the regulator. If no flow valve 46 is present, then the upstream orifice 62 of the gas flow inlet conduit 30 can be in gas-tight engagement with the pressurized gas system at any point downstream of the pressure valve 42. If no regulator 12 is present, as is the case with an oxygen concentrator, a humidifier, or the outlet of an institutional gas system, then the upstream orifice 62 of the gas flow inlet conduit 30 can be in gas-tight engagement with the pressurized gas system at any point upstream of an end use appliance 16.

The gas flow outlet 58 of the gas flow sensor 48 or gas flow switch 52 is in gas-tight engagement with the upstream orifice 66 of the gas flow outlet conduit 32, which conducts the pressurized gas column 34 away from the internal cavity 54 of the flow switch 52. The gas flow outlet conduit 32 also includes a downstream orifice 68 in gas-tight engagement with the pressurized gas system at any point downstream of the gas flow switch 52. In the example illustrated if FIG. 2, the downstream orifice 68 of the gas flow outlet conduit 32 is mounted via a gas tight connector 70 to a gas line 14 leading to an appliance 16.

In operation, the column of pressurized gas 34 enters the internal cavity 54 of the gas flow switch 52 via the gas flow inlet conduit 30, actuates the gas flow sensor (not shown), and exits the internal cavity 54 via the gas flow outlet conduit 32.

The gas flow inlet conduit 30 and the gas flow outlet conduit 32 can be composed of metallic or rigid plastic tubing or of flexible plastic tubing. Metallic or rigid plastic tubing is preferable where the alarm device 20 is stably or permanently attached to a regulator or other gas outlet, or where durability and longevity of the attachment is desired. Suitable materials include but are not limited to brass, aluminum, steel or steel alloy, or nylon, Flexible plastic tubing is preferable where flexibility of attachment is more important than stability, or where durability and longevity are of lesser importance. Flexible plastic tubing compositions can include for example polypropylene, silicone, and polyethylene. It will be understood that the choice of tubing composition will depend in part on compatibility with the gas being conveyed.

For metallic or rigid plastic tubing, the gas-tight connection between the gas flow inlet conduit 30 and the gas flow inlet 56 of the gas flow sensor 48 or gas flow switch 52 is preferably made by a complementary screw threaded connection. A similar connection is preferably employed in the gas tight connection between the gas flow outlet 58 and the gas flow outlet 32. A similar connection is preferably employed in the gas-tight connection between the gas flow outlet 58 and the gas flow outlet conduit 32. The gas-tight connections of the orifices 62 and 68 of conduits 30 and 32 to the pressurized gas system up and downstream from the gas flow switch 52 can by made by any gas-tight sealing mechanism known in the art, such as a locking ring and silicone or rubber seal (not shown). For flexible plastic tubing, all connections between the gas flow inlet conduit 30, the gas flow inlet 56, the gas flow outlet conduit 32, the gas flow outlet 58, and the pressurized gas system, are preferably made by means of suitable plastic or metallic barbed fittings, push-to-connect fittings, compression fittings, or cam and groove couplings well known in the art. It will be understood that in embodiments of the invention intended for use with oxygen, all components coming into contact with oxygen will be oxygen-clean. In general, all components coming into contact with any gas or other fluid in the pressurized system will be constructed of materials compatible with that gas or fluid, with respect to flammability, chemical reactivity, and toxicity.

The gas flow switch 52 or other gas flow sensor 58 can alternatively connect directly to the regulator 12, and to downstream points of the pressurized gas system, without the intervention of conduits (not shown).

Preferably the gas flow switch 52 is a direct flow sensing switch wherein a sensor element is situated directly in the column of pressurized gas 34 moving through the pressurized gas system. One type of sensor is the piston type, whose displacement by gas flow completes an electrical circuit to generate an error signal when the gas flow rate is above or below a predetermined flow rate. Preferably the gas flow switch 52 is an FS-926 Piston Type Flow Switch (Gems Sensors, Plainville Conn.). Suitable alternatives include but are not limited to the Ameritrol IX Series Inline Flow Switch, a calorimetric type, which measures the cooling effect of a gas as it passes over a sensor (Ameritrol, Vista, Calif.). Appropriate flow rates are determined by the user according to the type and purpose of the pressurized gas system. For a medical oxygen cannula, a flow rate of 0.25 to 15 liters per minute (0.0088 to 0.5296 standard cubic feet per minute) may be appropriate. Alternatively, the gas flow switch 52 can include, but is not limited to, a mass flow sensor and a reed switch sensor.

Figure 3:
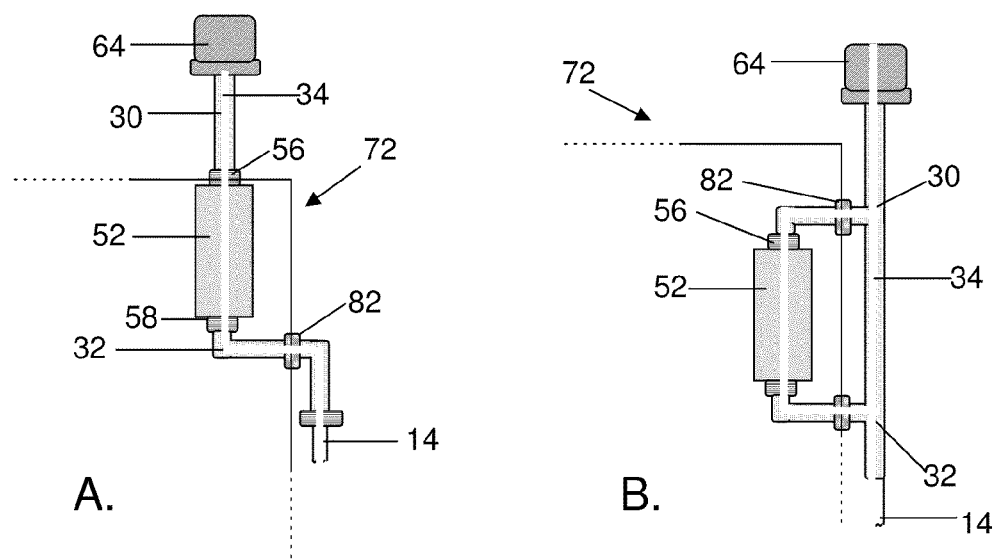
FIG. 3A shows a front elevation of a conduit configured to permit the inclusion of a straight gas flow switch into the present invention.
FIG. 3B shows a front elevation of a conduit configured to permit the inclusion of a bypass gas flow switch in the present invention.

The FS-926 gas flow switch is an angled body switch, that is, the column of pressurized gas 34 makes a right angle turn as it passes through the switch. The device of the present invention can also accommodate straight flow switches, wherein the column of pressurized gas 34 passes through the switch in a straight line (FIG. 3A), and also bypass switches, wherein only a portion of the column 34 is diverted through the switch (FIG. 3B). These accommodations can be made with minor adjustments of the geometry of the gas flow inlet conduit 30 and gas flow outlet conduit 32, as illustrated in FIGS. 1 and 3.

Flow sensors employing other types of sensing mechanisms can alternatively be employed, such as paddle, propeller, vane, and shuttle type sensors, a mass flow type sensor, a reed switch sensor, a calorimetric sensor and sensors that detect flow indirectly according to upstream and downstream pressure differences, such as a Bernouli sensor (not shown). A gas flow sensor 48 separate from the error signal generator 50 (FIG. 1) can be included to provide greater versatility than the gas flow switch 52. For example, the device can include a gas flow sensor 48 producing different signals in response to abnormally low gas flow and abnormally high gas flow. Such a sensor can provide distinctive alarm indications for a loss of gas flow, as would be expected downstream from a gas line blockage, disconnection, or cylinder depletion, and for high gas flow, as would be expected upstream of the disconnection of a end use appliance 16, depending upon where the gas flow sensor 48 is located. A gas flow sensor 48 which quantitates levels of gas flow, rather than simply detecting violations of flow limits, can alternatively be included, to provide continuous data on flow rate, in addition to an alarm indication. One example is the FS1015 Series mass flow sensor (Siargo Ltd., Santa Clara, Calif.). Another is the Honeywell Zephyr™ Digital Airflow Sensor, HAF Series (Honeywell Sensing and Control, Golden Valley, Minn.). Such sensors have the greatest utility when included in embodiments of the present invention that also include a microcontroller, to be described below.

The present invention includes at least one housing 72 having a top wall 74, a bottom wall 76, two opposite side walls 78, and opposite front and rear walls (not shown), and defining an interior space 80. The housing contains the flow sensing and error signaling subassembly 22 or at least the gas flow sensor 48 thereof, and the power subassembly 28. Apertures equipped with bushings 82 or other securing mechanism known can be in the art can be defined in any wall of the housing 72 to allow portions of the gas flow sensing and error signaling subassembly 22 to protrude from the interior space 80 into the exterior of the housing. Potentially protrusive portions include the gas flow inlet 56, the gas flow outlet 58, the gas flow inlet conduit 30, and the gas flow outlet conduit 32, as illustrated in FIG. 3.

The housing 72 also contains the power subassembly 28 and the indicator subassembly 24. The power subassembly 28 includes a power source 84, preferably including at least one battery 86 enclosed in a battery compartment 88 and mounted in battery clip 90, the battery compartment being attached to any convenient wall of the housing 72. The voltage and capacity of the battery will depend on the number and type of included indicator mechanisms 26 and microcontrollers 104, to be described below. A single nine volt alkaline battery is suitable many embodiments. Alternative power sources include, but are not limited to, built-in rechargeable NiCD or NiMH batteries, DC current, AC house current delivered via a DC step down transformer (not shown) and a solar cell (not shown). The power subassembly 28 also includes a master power switch 92 to activate and completely inactivate the alarm device 20. The master power switch can include any lever, toggle, or button type known in the art, to completely activate or deactivate the device. The master power switch 92 can be secured by a lock and operated by a lock and key 93, to prevent deactivation of the alarm device 20 by unauthorized personnel. A power light 95, activatable by the master power switch 92, can be included to inform users of the power status of the device 20.

The indicator subassembly 24 includes at least one indicator mechanism 26 operatively connected to the flow sensor and error generator subassembly 22, the indicator mechanism 26 being activatable by an error signal to produce at least one alarm indication perceptible to a user or a device.

Indicator mechanisms 26 can include but are not limited to an audio alarm tone producer 94 such as a bell, a mechanical buzzer, and electronic tone synthesizer. Indicator mechanisms 26 can include a visual display 96 such as an incandescent lamp, a fluorescent tube, a light emitting diode or a liquid crystal display. Indicator mechanisms 26 can include a broadcast signal transmitter 98, defined as a transmitter to communicate an alarm signal to at least one remote receiver 100 to elicit a final alarm indication in the remote receiver. Broadcast signal transmitters 98 can include but are not limited to an radio transmitter broadcasting on AM, FM, or other broadcast radio frequency, to communicate with a radio receiver; a telephone transmitter, to communicate with a telephone receiver via a telephone line or to a cellular phone or pager through a cellular phone network; a wireless local area network (LAN) router to communicate with a computer or other device equipped with a wireless receiver; an Ethernet® router, to communicate with devices on the same wired LAN; a transmitter employing the Bluetooth™ protocol to communicate with a cellular phone, printer, or other Bluetooth™ equipped device; a closed circuit intercom base station to communicate by wire with an intercom substation; and a signal generator to transmit a signal perceivable by a remote-controlled reservoir-changing device regulator, the signal triggering the reservoir changing device to open a fresh cylinder 10 or other reservoir to the pressurized gas system. The remote control reservoir changing device can be a device provided by the present invention, as will be discussed, or any other suitable device known in the art. The broadcast signal transmitter 98 can include a pilot light 99 to indicate that the transmitter 98 has been activated.

In operation, when the gas flow switch 52 senses a gas flow rate violating a predetermined limit, it closes a circuit to direct current toward at least one of the indicator mechanisms 26, thereby actuating the indicator mechanism 26 to produce an alarm indication. The electrical connections between the power subassembly 28, the flow switch 52, the indicator mechanisms 26, and all additional components described below, are generally defined as connection means 40 in the Figures. It will be understood that particular configurations of connection means such as wiring or printed circuitry will be determined by well known principles of circuit design according to the type of gas flow sensor 48, error signal generator 50, indicator mechanisms 26, and power source 84 selected by a user.

The indicator subassembly 24 can also include a silencing switch 102 whose actuation deactivates at least one activated indicator mechanism 26. The silencing switch 102 permits a user to turn off an alarm indication without having to deactivate the master power of the alarm device 20. The silencing switch 102 can be interposed between an indicator mechanism 26 and the power source, as illustrated in FIG. 1, or it can be situated in any relation to an indicator mechanism 26 that permits deactivation of that indicator mechanism 26. The silencing switch 102 is preferably a key-controlled switch to prevent unauthorized personnel from silencing the indicator mechanism 26. The key control is preferably of the mechanical lock and key type (not shown) but it can alternatively include a more complex system such as a magnetic card and swiper combination. Preferably there is operatively connected to the silencing switch a silencing switch indicator 103, such as a lamp, which is activatable by the activation of the silencing switch 102. The silencing switch indicator 103 reminds a user that an indicator mechanism 26 has been shut off.

The indicators mechanisms 26 and silencing switch 102 can be disposed in any convenient position in the housing 72. Preferably they are visible to a user through suitable apertures or windows in the front wall (not shown) of the housing 72.

Figure 4:
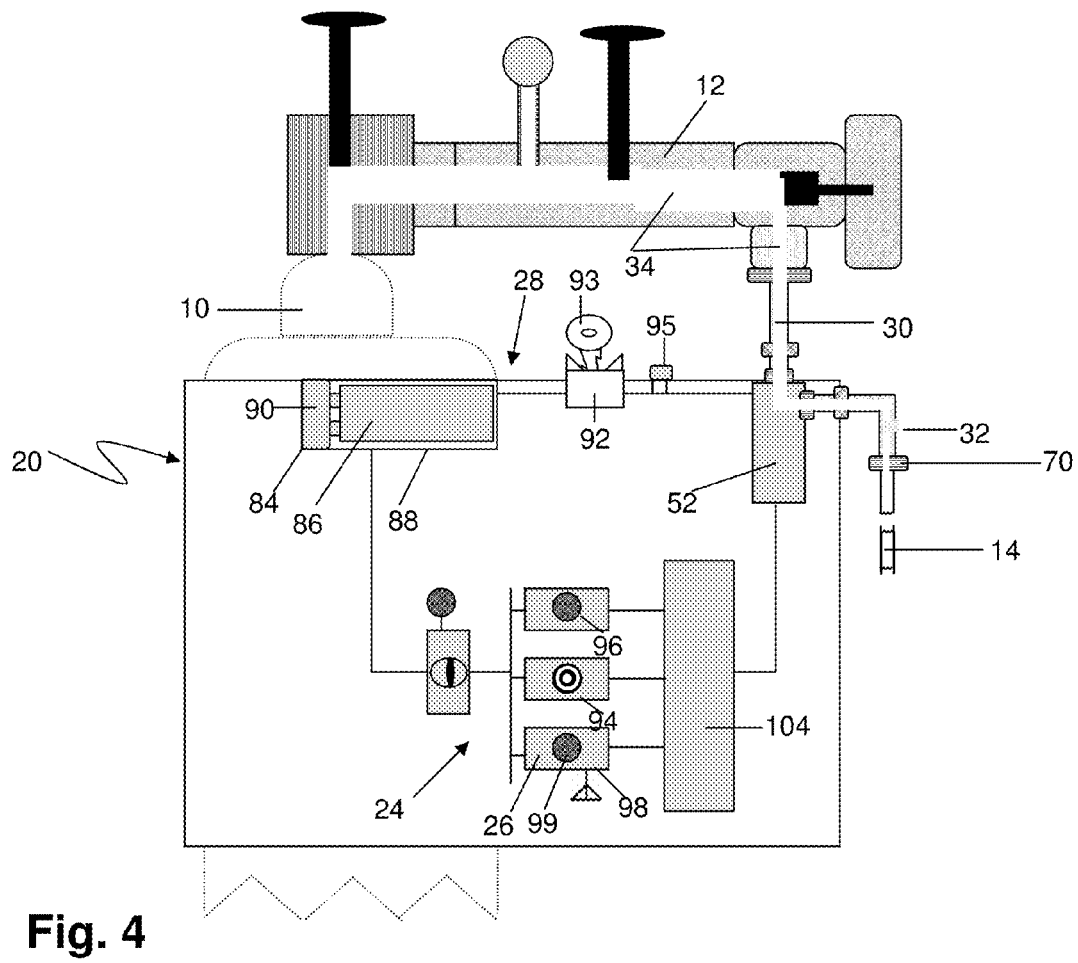
FIG. 4 shows a frontal semi-schematic view of the alarm device including a microcontroller.

The indicator subassembly 24 can also include at least one microcontroller 104 operatively connected to the gas flow switch 52, or other error signal generator 50, and to at least one indicator mechanism 26, as illustrated in FIG. 4. The microcontroller 104 is programmed with at least one routine activatable on receipt of an error signal from the flow switch 52. On activation, the routine commands at least one indicator mechanism 26 to produce an alarm indication. The addition of a microcontroller 104 to the alarm device 20 can add great variety to the alarm indications. The microcontroller 104 can be programmed with routines to vary the sound, frequency pattern, and intermittence of an audio alarm tone producer 94, thereby generating beeps, warbles, synthesized words, and the like. Routines can include commands to a visual display 96 to produce displays such as flashing lights, an ordered display of multiple LED's, or a text message via liquid crystal display. Routines can include commands to a broadcast signal transmitter 98 to transmit to a remote receiver 100 a text or voice message regarding, for example, the location of the pressurized gas system experiencing a gas flow malfunction. In embodiments of the warning device including a gas flow sensor 48 that provides quantitative gas flow data, the microprocessor 104 can include routines that command the digital display of gas flow values. Microcontrollers 104 can be purchased preprogrammed with suitable routines, or can be programmed by the fabricator of the warning device or by the end user. Suitable microcontrollers are available from Maxim Integrated Products, Sunnyvale, Calif.

Figure 5:
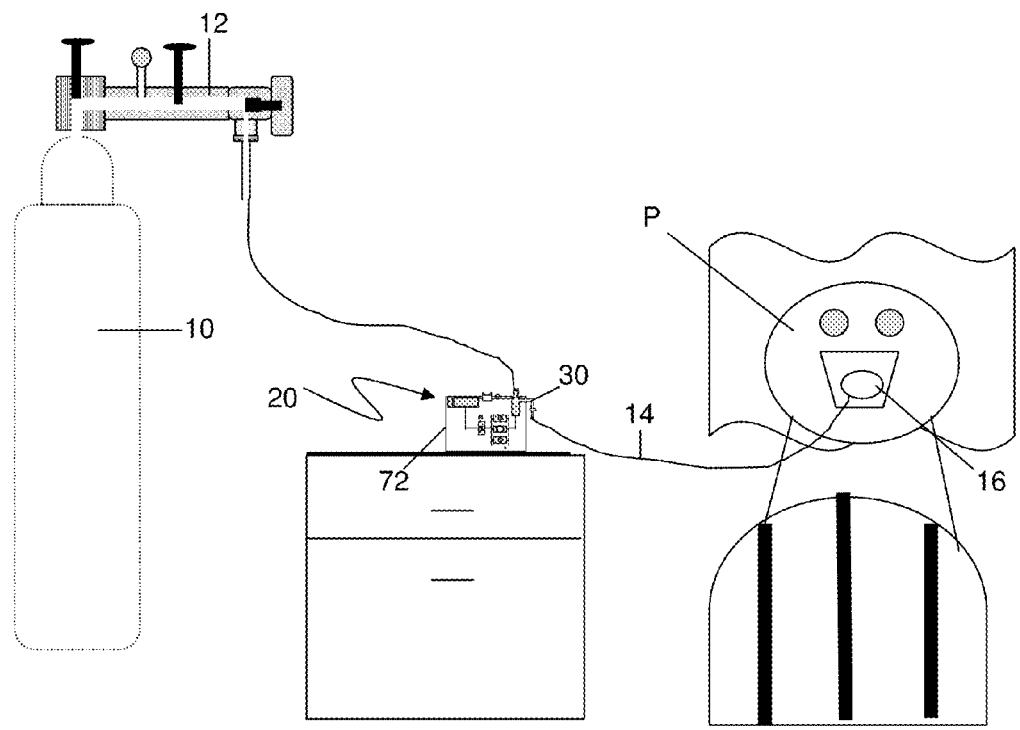
FIG. 5 shows a frontal semi-schematic view of the alarm device situated on a tabletop.

The housing 72 containing the alarm device 20 can be located in any convenient spatial situation relative to the gas cylinder 10 and the end use appliance 16. The housing 72 can for example rest on a table top, situated near the end user, such as an oxygen therapy patient (P), as illustrated in FIG. 5. Alternatively, the housing 72 can be mounted upon a regulator 12 by means of a shelf, a railing, brackets, or chains (not shown). It can be mounted upon an oxygen cylinder, upon the cart of a portable oxygen cylinder, upon a flow meter, or upon a humidifier (not shown). If the warning device 20 is of sufficiently lightweight construction, then the housing 72 can depend from the regulator outlet 64, with its weight supported by the gas flow inlet conduit 30 (not shown). The housing 72 can be incorporated into a gas regulator 12 during fabrication of the regulator (not shown). Hardware and design appropriate for these situations are well known.

Figure 6:
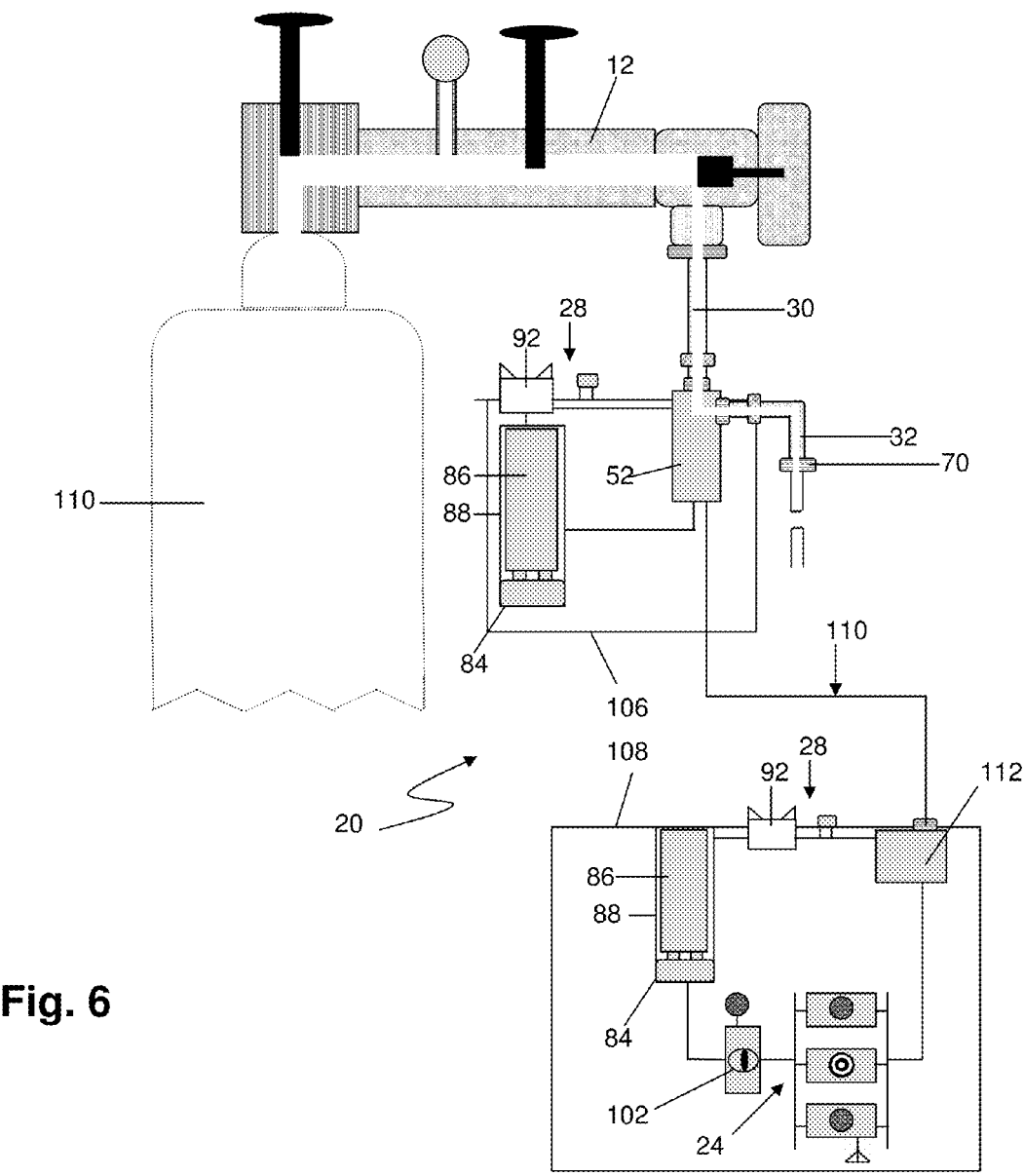
FIG. 6 shows a frontal semi-schematic view of an embodiment of the alarm device housed in a primary and a remote housing, with communication between housings mediated by a wired connection.
Figure 7:
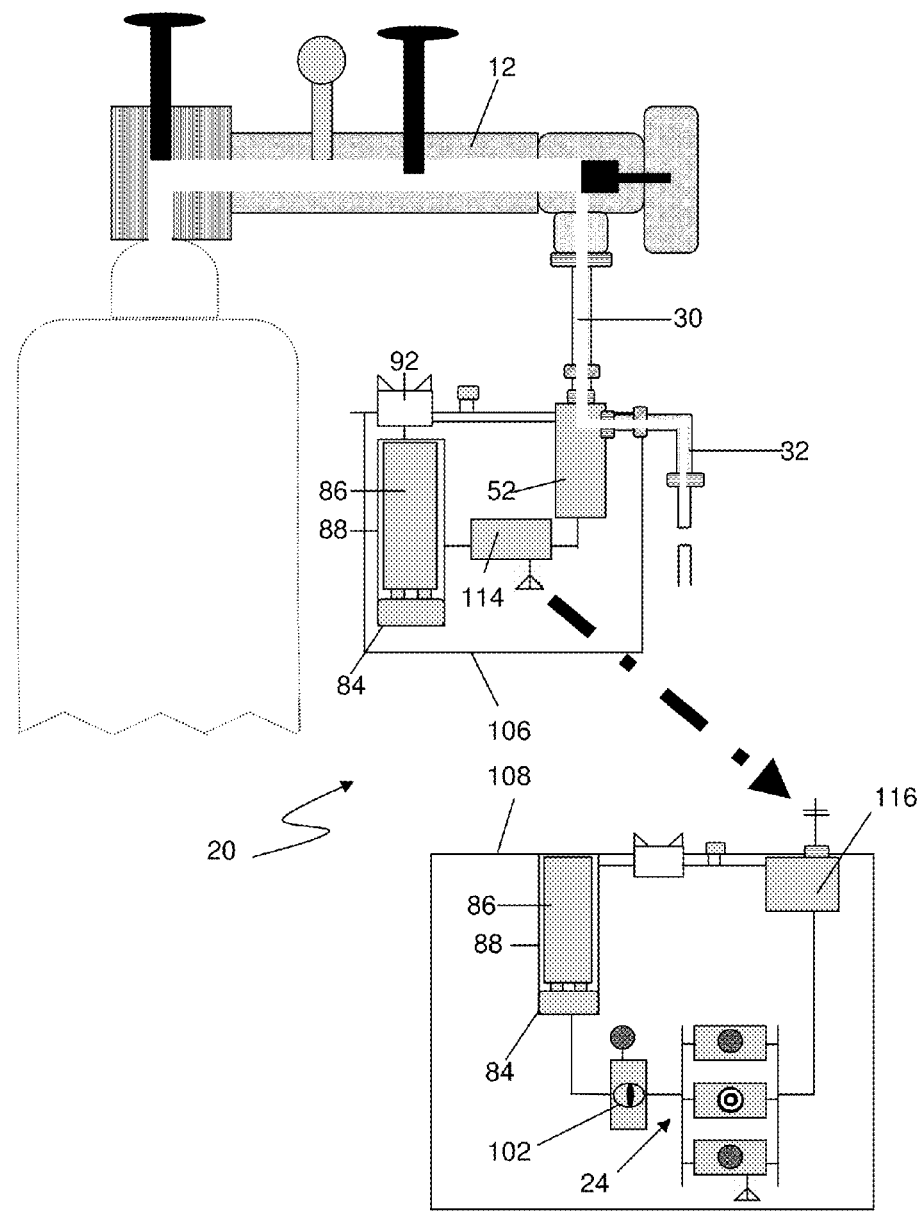
FIG. 7 shows a frontal semi-schematic view of an embodiment of the alarm device contained in a primary and a remote housing, with communication between housings mediated by wireless communication, with the dashed arrow indicating a route of wireless communication.

The present invention can be contained in multiple housings, including a primary housing 106 to contain at least a gas flow sensor 48 and a power subassembly 28, and at least one remote housing 108 to contain at least an indicator subassembly 24. An advantage of a multiple housing configuration is the capability of situating the flow sensing and error signaling subassembly 22, or components thereof, in a primary housing 106 situated in proximity to a gas regulator 12; and situating the indicator subassembly 24 at a site more convenient for monitoring the pressurized gas system. The remote housing 108 can include a separate power system 28 to provide power to the indicator subassembly 24. An example of multiple housing embodiment of the alarm device 20, configured for a medical gas system, is illustrated in FIGS. 6 and 7. The signal from the gas flow switch 52 or other error signal generator (not shown), contained in the primary housing 106, can be conveyed to the indicator subassembly 24, contained in the remote housing 108, by means of a wired connection 110 to the indicator subassembly 24 or to an intermediate receiver 112 in operative connection to the indicator subassembly 24, in the manner of a wired closed circuit intercom or telephone (FIG. 6). Alternatively, the gas flow switch 52 can be operatively connected to a wireless transmitter 114 in the primary housing 106, which conveys a signal via a wireless connection (dashed arrow) to a wireless receiver 116, contained in the remote housing 108, and in operative connection to the indicator subassembly 24 (FIG. 7). Any known transmitting and receiving technology such as AM radio transmission can be utilized to convey the signal.

To provide advance warning of the depletion of a gas in a cylinder 10 or other pressurized reservoir, the warning device 20 can also include a reservoir pressure sensing and pressure error signal generating subassembly to produce an alarm indication when the gas pressure in pressurized reservoir falls below a predetermined limit. The reservoir pressure sensing and pressure error signal generating subassembly is preferably incorporated into a gas pressure switch 124, preferably located upstream of the pressure valve 42 of a regulator 12, where reservoir pressure is most reliably determined. Alternatively, a separate gas reservoir pressure sensor and pressure error signal generator (not shown) in lieu of the gas pressure switch 124.

Figure 8:
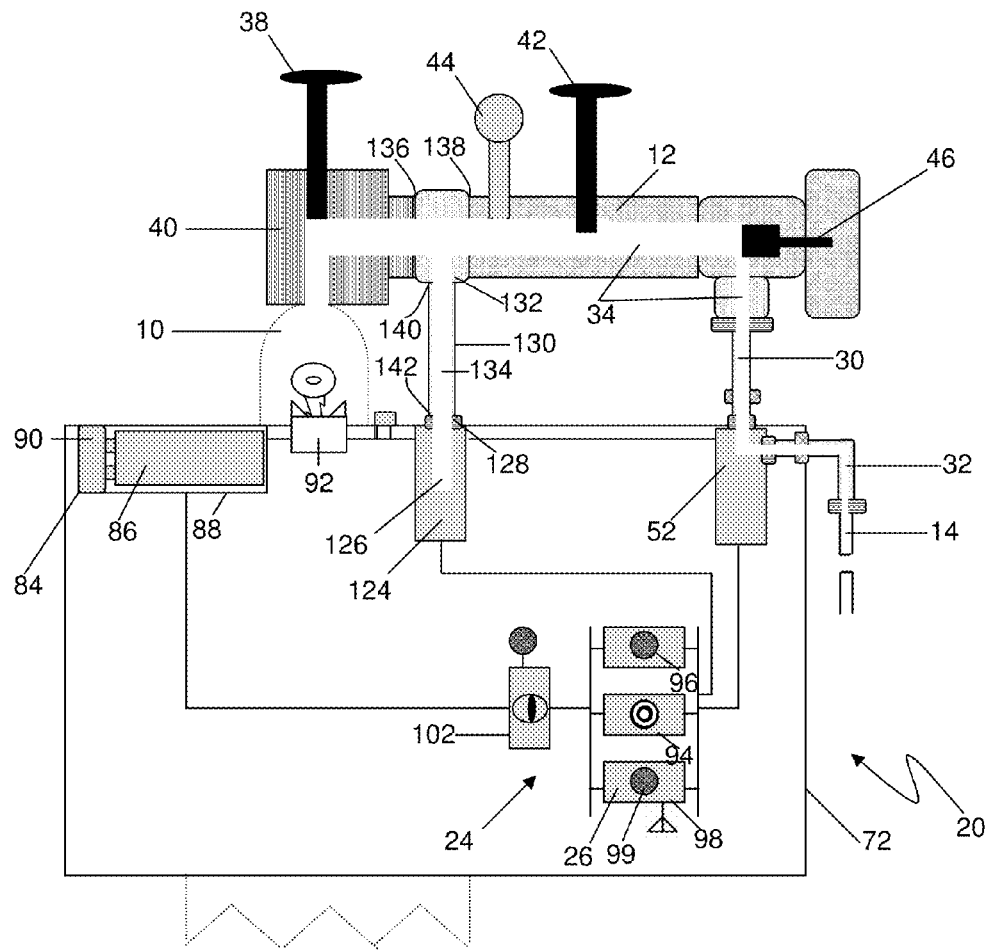
FIG. 8 shows a frontal semi-schematic view of an embodiment of the alarm device additionally including a gas pressure switch.

The addition of reservoir pressure sensing capability can provide earlier warning of the depletion of, for example, a medical oxygen cylinder. An alarm device that senses gas flow malfunctions downstream of the flow valve 46 of a regulator 12 does provide an alarm indication in response to cylinder depletion, but only when depletion has become severe enough to affect gas flow. A gas pressure switch 124 that senses reservoir pressure can be set to generate an error signal before depletion reaches that level of severity. Such a gas pressure switch 124, however, must be situated upstream of the pressure valve 42, where pressure is most reliably sensed, so it is insensitive to malfunctions in the gas line downstream of the flow valve. 46. The combination of a gas pressure switch 124, and a gas flow switch 52, situated as in FIG. 8, provides warning capabilities that cover all possible malfunctions that can afflict a pressurized gas system.

Preferably, the gas pressure switch 124 is a commercial gas pressure switch, most preferably the J205G/J205LG overpressure switch (Whitman Controls Corp, Bristol Conn.), which is of the electronic pressure plate type, and GEMS 3100 pressure series switches (Gems Sensors, Plainville Conn.), which are solid state pressure switches that sense pressure by means of a strain gauge diaphragm. Other types of gas pressure switch can alternatively be included, such as a spring loaded piston switch.

The gas pressure switch 124 includes an internal cavity 126 containing the pressure plate or other sensor mechanism (not shown) and communicating with the pressurized gas system via a gas pressure inlet 128. The gas pressure inlet 128 can be connected to the pressurized gas system by any means of gas-tight engagement known in the art. Preferably the gas pressure switch 124 or other pressure sensor is connected to the pressurized gas system via a gas pressure conduit 130 to expose the gas pressure switch 124 to the internal pressure of the cylinder 10. The gas pressure conduit 130 can be of any form which connects the gas pressure switch 124 in gas-tight engagement with the cylinder 10. In the example illustrated in FIG. 8, the gas pressure conduit 130 includes a tubular adaptor member 132 situated perpendicular to a tubular conduit member 134. The adaptor member 132 intervenes between the cylinder connector 40 and the regulator 12, and includes an upstream orifice 136 in gas-tight engagement with the cylinder connector 40, a downstream orifice 138 parallel to the upstream orifice 136, in gas tight engagement with a regulator 12, and a conduit orifice 140 perpendicular to the upstream and downstream orifices, 136 and 138. The conduit orifice 140 is in gas-tight engagement with the proximal end of the conduit member 134. The distal end of the conduit member 134 includes a sensor orifice 142 in gas tight engagement with the gas pressure inlet 128 of the gas pressure switch 124 or other gas pressure sensor. The gas-tight connections between the gas pressure inlet 128 and the gas pressure conduit 130, and between the gas pressure conduit 130, cylinder connector 40, and regulator 12, are preferably made by complementary screw threaded connections.

Alternatively, the gas pressure switch 125 can be engaged to the pressurized gas system at any point at which cylinder pressure can be accurately sensed. The gas pressure switch can, for example, be incorporated into the cylinder pressure gauge 44.

Figure 9:
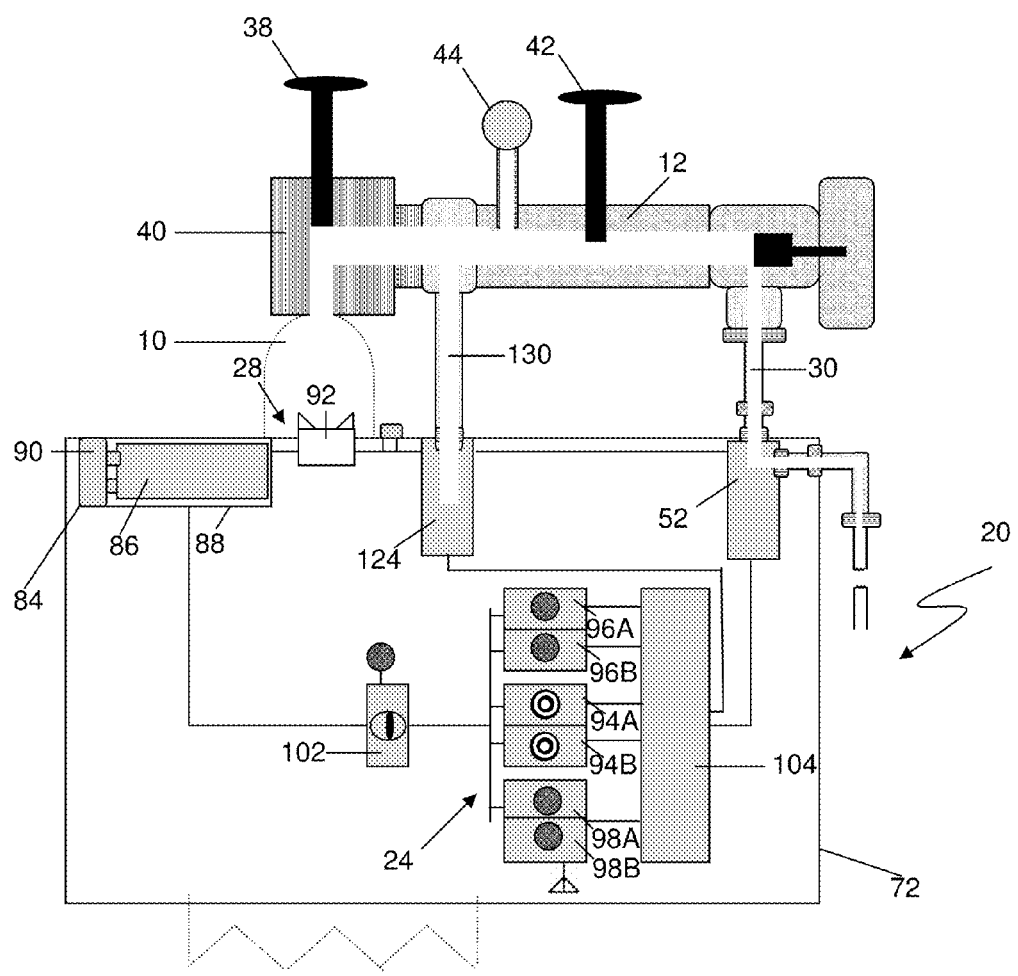
FIG. 9. shows a frontal semi-schematic view of an embodiment of the alarm device including gas pressure switch, and additionally including a microcontroller.

Preferably, the gas pressure switch 124 and gas flow switch 52 are in operative engagement with a common indicator subassembly 24 and a common silencing switch 102, as illustrated in FIGS. 8 and 9. Alternatively, the gas pressure switch 124 is in operative engagement with a separate gas pressure indicator subassembly (not shown). The gas pressure switch 124 can be powered by the same power subassembly 28 as the gas flow switch 52, as illustrated in FIGS. 8 and 9, or it can be powered by a separate power subassembly (not shown). In operation, the gas pressure switch 124, exposed to the gas pressure of the cylinder 10 senses a gas pressure below a predetermined limit and closes a circuit to direct an error signal to at least one of the indicator mechanisms 26 of the indicator subassembly 24, thereby actuating the indicator mechanism 26 to produce an alarm indication. The indicator subassembly 24 can be configured to direct a gas pressure error signal and a gas flow error signal to different indicator mechanisms 26. In this configuration, the alarm device 20 can inform a user whether an alarm indication was triggered by abnormal reservoir pressure or by a gas flow malfunction downstream of the regulator 12. This differential indication is most readily accomplished if a microcontroller 104 is included to issue different gas flow and pressure flow error commands to the indicator subassembly 24, or to route commands to different indicator mechanisms 26, or both. FIG. 9 illustrates an alarm device 20 capable of producing distinctive gas flow pressure alarm indications via gas flow specific indicating devices (94A, audio, 96A, visual, 98A, broadcast), and gas pressure indicating devices alarm indications (devices (94B, audio, 96B, visual, 98B, broadcast).

Figure 10:
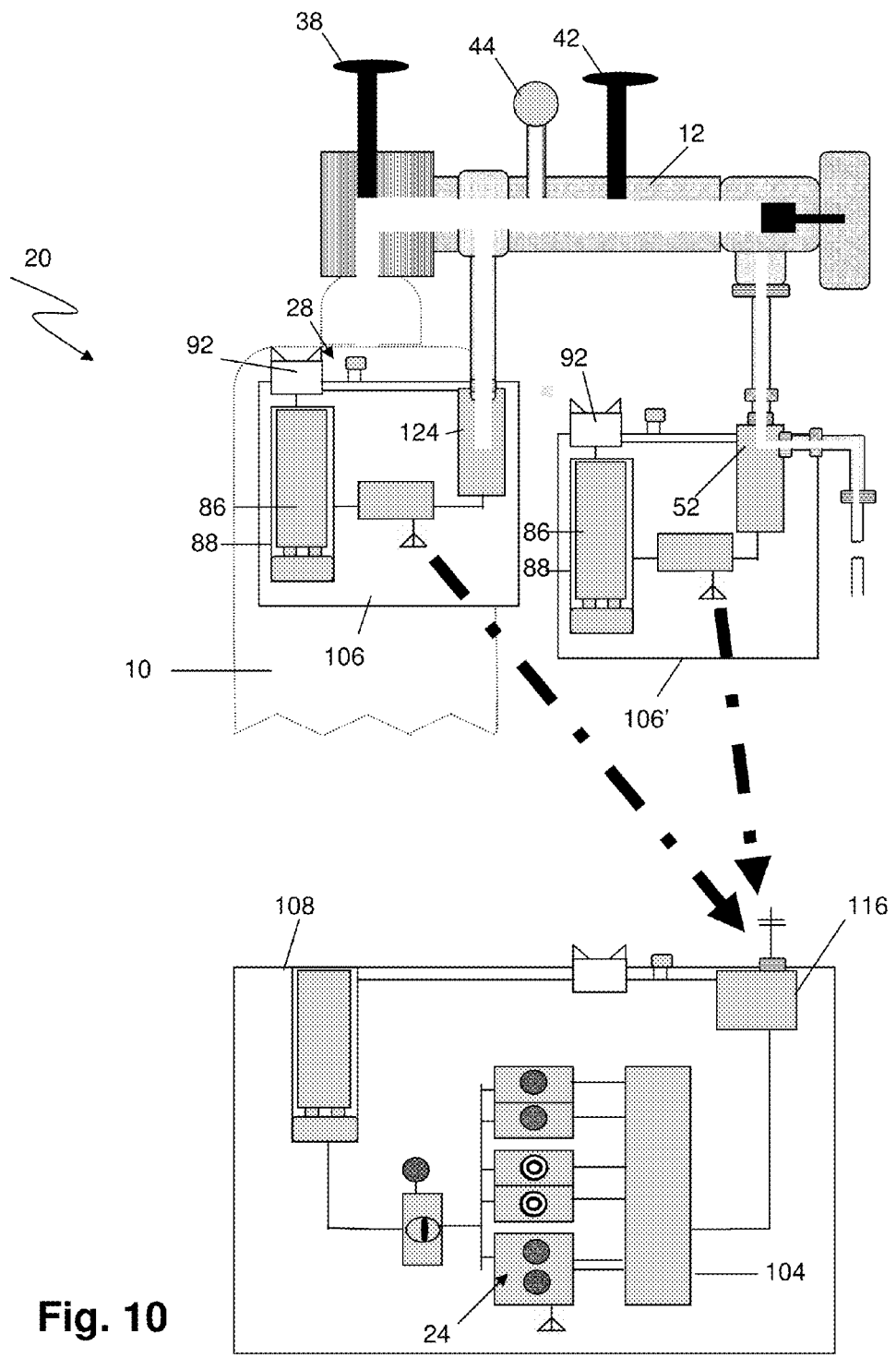
FIG. 10 shows a frontal semi-schematic view of an embodiment of the warning alarm device contained in two primary housings and one remote housing, with communication between primary housings and remote housing mediated by wireless communication, with the dashed arrows indicating a route of wireless communication.

The gas pressure switch 124, or other reservoir pressure sensing and error signal generating subassembly, can be contained in the same housing 72 as the gas flow switch 52, as illustrated in FIGS. 8 and 9. Alternatively, they can be contained in multiple housings. In the example illustrated in FIG. 10, a primary housing 106 contains at least a flow switch 124 and a power subassembly 28. A remote housing 108 contains at least an indicator subassembly 24. Communication between the gas pressure switch 124 and the indicator subassembly 24 can be by wireless broadcast, as illustrated for example in FIG. 10, by wire, or by any suitable form of remote communication, as previously described. Any conceivable combination of primary and remote housings 106, 108 is encompassed by the present invention. In the example illustrated in FIG. 10, a gas pressure switch 124 is included in a first primary housing 106, and a gas flow switch is included in a second primary housing 106', with both switches communicating with a common indicator subassembly 24 in a remote housing 108.

The present invention also includes embodiments including a gas pressure switch 124, or other reservoir pressure sensing and error signal generating subassembly, and not including a gas flow switch 52 or other gas flow sensing and error signal generating subassembly.

Figure 11:
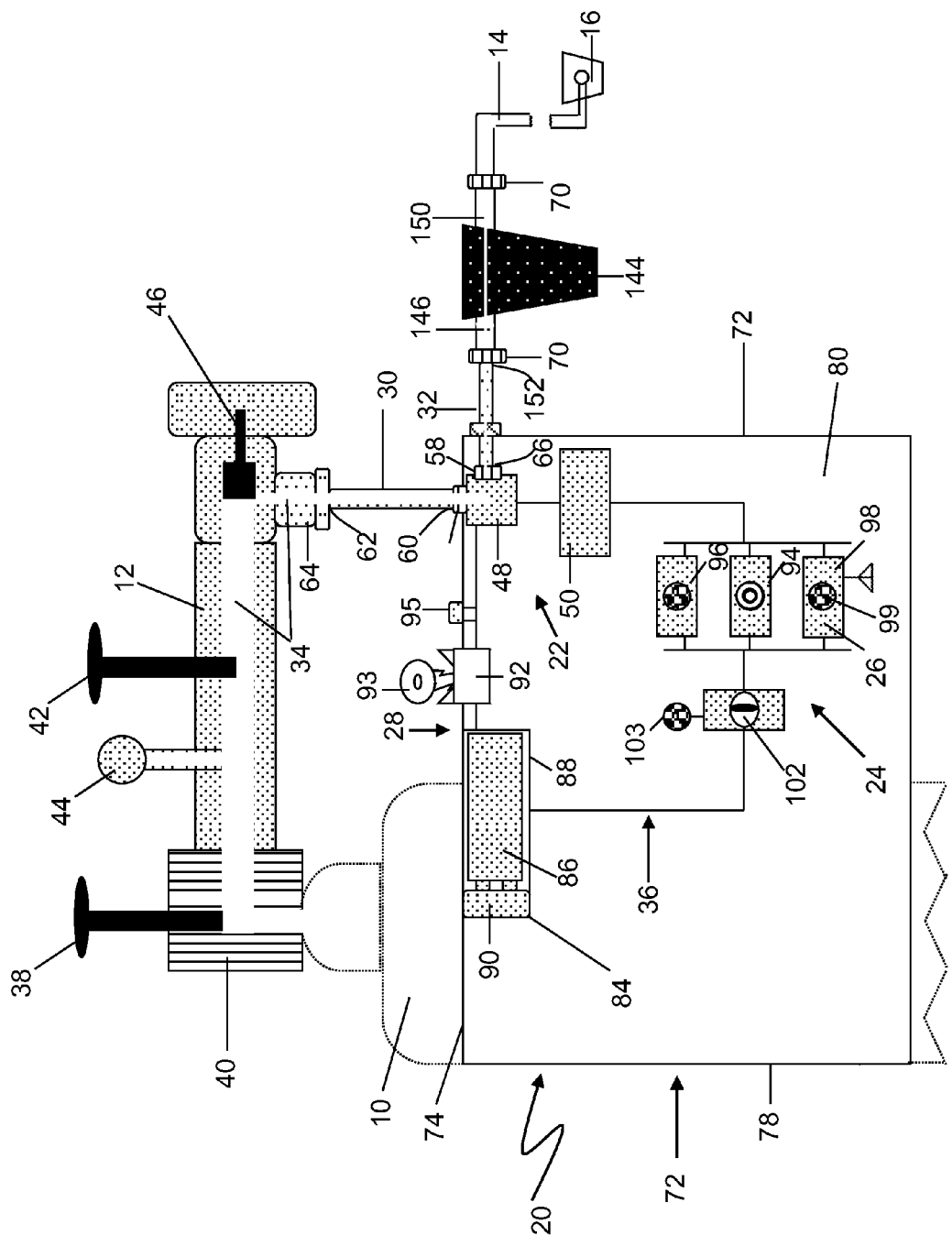
FIG. 11 shows a frontal semi-schematic detail view of an embodiment of the warning alarm device including a downstream accessory device situated externally to the housing of the device.
Figure 12:
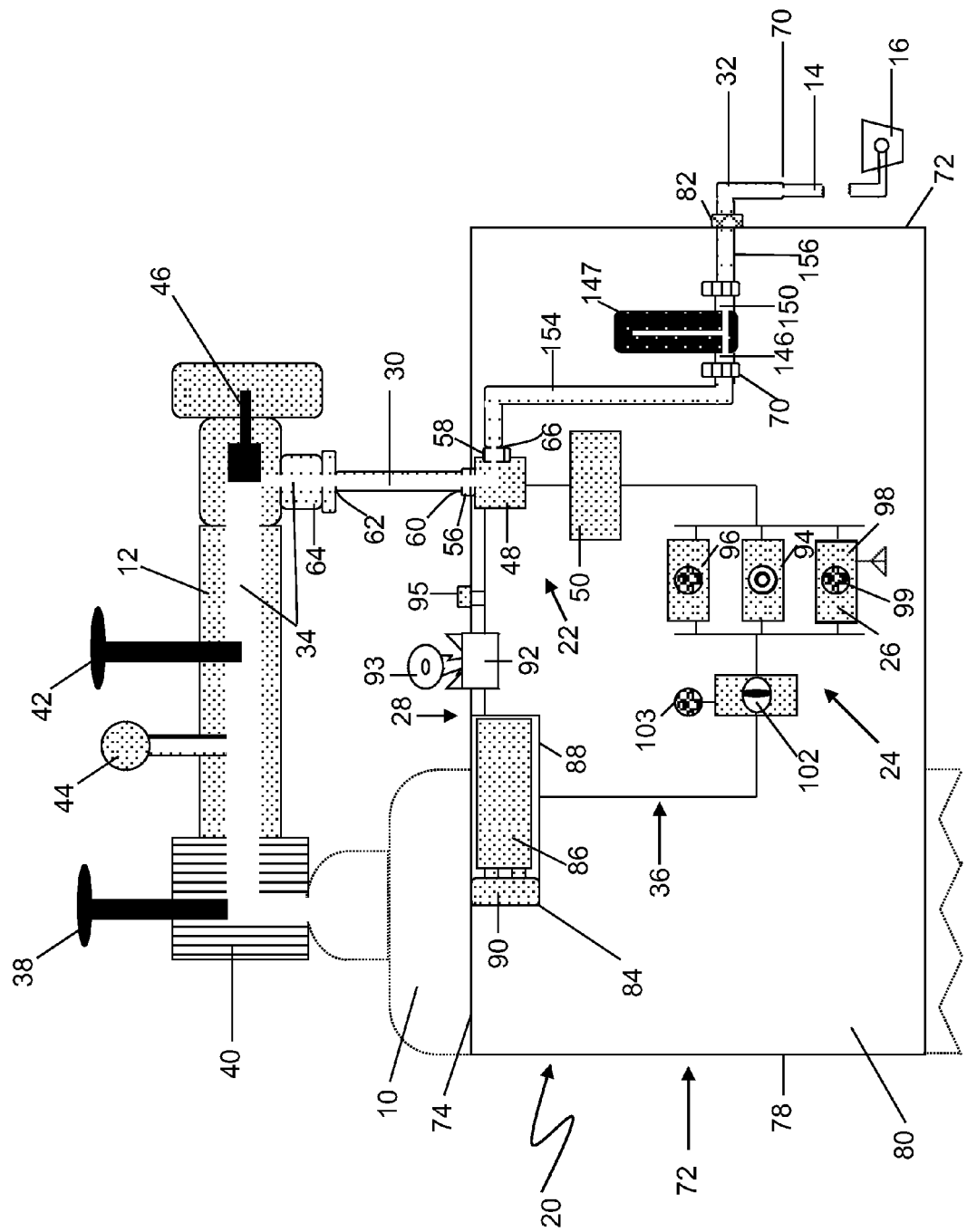
FIG. 12 shows a frontal semi-schematic detail view of the warning alarm device including a downstream accessory device within the housing of the device.

The present invention can additionally include at least one downstream accessory device 144, as illustrated in FIGS. 11 to 14, the downstream accessory device 144 having at least an upstream port 146 in gas-tight engagement with the gas flow outlet conduit 32. For a medical oxygen system, the downstream accessory device 144 can include a filter (not shown), a humidifier (not shown), a flow meter 147, or an oxygen analyzer 148. A downstream accessory device 144 including a filter, humidifier, or flow meter 147 is preferably engaged with the gas flow outlet conduit 32 in a linear relationship, that is, with the entire pressurized gas column 34 passing into the upstream port 146 and out of the downstream port 150 of the downstream accessory device 144, as illustrated in FIG. 11. The upstream port of a downstream accessory device 144 including a filter, humidifier, or flow meter is preferably engaged to a portion of the gas flow outlet conduit 32 external to the housing 72, so that the filter material or humidifier fluid can easily be accessed for replenishment, and the display of the flow meter 147 can easily be observed. For example, a filter or humidifier can be in gas-tight engagement with the distal end 152 of the gas flow outlet conduit 32 by means of any gas-tight connector 70 known in the art, and the downstream port 150 can be in gas-tight engagement with a gas line 14. A downstream accessory device 144 including a flow meter 147 can also be situated external to the housing 72, so that its flow rate display is readily visible to a user. A flow meter 147 can alternatively be situated within the interior space 80 of the housing 72, as illustrated in FIG. 12. In this situation, the gas flow outlet conduit 32 includes a proximal member 154 and a distal member 156. The upstream port 146 of the downstream accessory device 144 is in gas-tight engagement with the proximal member 154 of the gas flow outlet conduit 32, and the downstream port 150 of the downstream accessory device 144 is in gas-tight engagement with the distal member 156 of the gas flow outlet conduit 32. In this situation, the flow rate display of the flow meter 147 can be read by a user through a flow meter window (not shown) defined in any wall of the housing 72.

Figure 13:
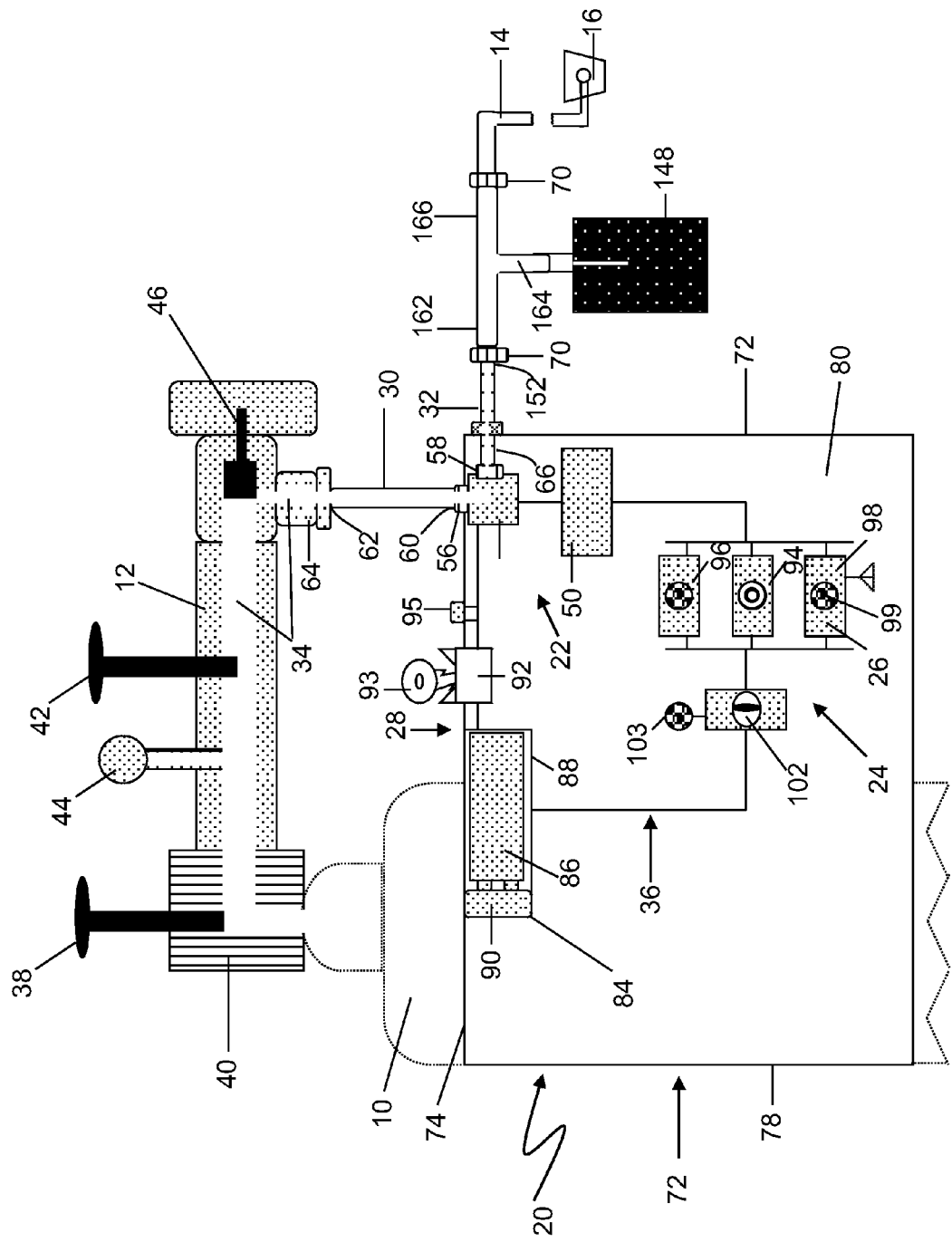
FIG. 13 shows a frontal semi-schematic detail view of the warning alarm device including a downstream oxygen analyzer situated externally to the housing of the device.

A downstream accessory device including an oxygen analyzer 148 having a port 158, the oxygen analyzer 148 is preferably engaged with the gas flow outlet conduit 32 in a bypass relationship, that is, with only a portion of the pressurized gas column 34 passing into the port 158 of the oxygen analyzer 148. As illustrated in FIG. 13, this situation can be achieved by means of a T-shaped connector 160 having an upstream port 162 in gas-tight engagement with the distal end 152 of the gas flow outlet conduit 32, a bypass port 164 in gas-tight engagement with the port 158 of the oxygen analyzer 148 and a downstream port 166 in gas-tight engagement with a gas line 14 or a downstream appliance 16. A valve (not shown) can be included in the bypass port 164 to admit the pressurized gas column 34 into the oxygen analyzer 148 only when desired by a user. The oxygen analyzer 148 and its T-shaped connector 160 can also be contained within the interior space 80 of the housing 72, in a situation similar to that illustrated for the flow meter 147 in FIG. 12.

Figure 14:
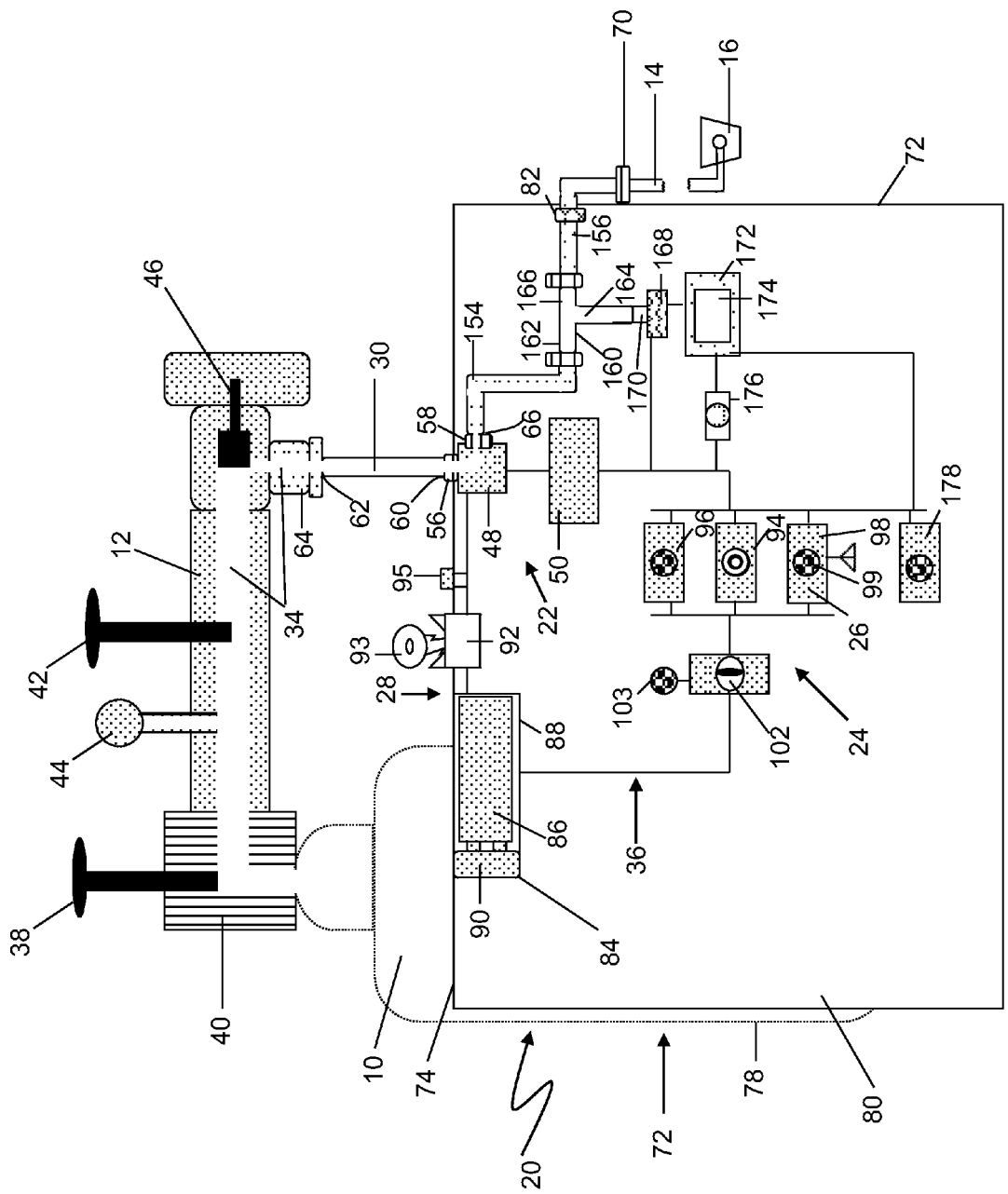
FIG. 14 shows a frontal semi-schematic detail view of the warning alarm device including an oxygen sensor.

Alternatively, the components of an oxygen analyzer can be incorporated directly into the alarm device 20. For example, as illustrated in FIG. 14, an oxygen sensor 168, to sense oxygen content in the pressurized gas stream 34, includes an inlet port 170 in gas-tight engagement with the bypass port 164 of the T shaped connector 160, whose upstream port 162 is in gas-tight engagement with the proximal member 154 of the gas flow outlet conduit 32 and whose downstream port 166 is in gas-tight engagement with the distal member 156 of the gas flow outlet conduit 32. Preferably the oxygen sensor 168 is of the electrogalvanic fuel cell type commonly employed in commercial oxygen analyzers. More preferably the oxygen sensor is a Teledyne R17MED (Teledyne, City of Industry, Calif.) electrogalvanic fuel cell, although any suitable type or model of oxygen sensor can be incorporated. The oxygen sensor 168, which produces a voltage proportional to the oxygen content of the pressurized gas column 34, is operatively engaged via connection means 36 to a voltmeter 172. The volt meter 172 is configured to measure the voltage produced by the oxygen sensor 168, calculate from that voltage a corresponding value of the percentage of oxygen in the pressurized gas column 34, and display that value on a digital display 174. The volt meter 172 can be calibrated by exposing the oxygen sensor 168 to air and to pure oxygen, in a procedure well known in the art. Air and pure oxygen can be introduced through the upstream orifice 62 of the gas flow inlet conduit 30. The oxygen sensor 168 additionally includes an oxygen sensor on-off button 176 to allow a user to activate the oxygen sensor 168 when a reading is desired. An on-off button aperture (not shown) is defined at any location in the housing 72 adjacent to the oxygen sensor on-off button 176. The oxygen sensor 168 can be anchored to any convenient wall of the housing 72 by suitable brackets or other anchoring means known in the art. As oxygen sensors of the electrogalvanic type become exhausted after many months of use, an oxygen sensor access hatch (not shown) can be included to allow a user to replace the oxygen sensor 168. The oxygen sensor hatch can be defined at any location on the housing 72 adjacent to the oxygen sensor 168.

The voltmeter 172 can additionally be configured to send an error signal to an $O_2$% alarm indicator 178 upon displaying a percent oxygen value below a predetermined limit. The $O_2$% alarm indicator 178 can include an alarm indicator of the audible, visual, or broadcast alarm type.

The present invention can additionally include at least one upstream accessory device (not shown), the upstream accessory device including a flow meter 147 or a humidifier (not shown). The upstream accessory device includes an upstream port (not shown) in gas tight engagement with a source of pressurized gas, and a downstream port (not shown) in gas-tight engagement with the gas flow inlet conduit 30 or with the gas flow inlet 56 of either the gas flow sensor 48 or the gas flow switch 52, the gas tight engagements being made by means of any gas-tight connector known in the art. The source of pressurized gas can include a regulator 12, an oxygen concentrator (not shown), or the outlet of an institutional gas supply (not shown). The downstream accessory device (not shown) can be situated either external or internal to the housing 72.

The present invention also provides a reservoir changing device, generally shown at 180 in FIGS. 15 to 19. The purpose of the reservoir changing device is to open a reserve cylinder 10", or other reserve reservoir of gas to a pressurized gas system upon receiving an alarm indication that pressure in a primary gas cylinder 10', or other primary reservoir, has fallen below a predetermined limit. The alarm indication can include any of the broadcast alarm indications generated by the alarm device 20 of the present invention, including embodiments either including or lacking a gas flow sensor 48 or gas flow switch 52. Alternatively, the alarm indication can be provided by additional or alternative indicator mechanisms (not shown). The reservoir changing device 180 is also useful in pressurized fluid systems other than gas systems.

The reservoir changing device 180 includes an adaptor 182 to connect the device 180 to a gas regulator 12 or other fluid distribution means, at least a first valve member 184 and a second valve member 186, each valve member being in gas-tight engagement with the adaptor 182, and also engageable with a cylinder 10', 10" or other gas reservoir. The first and second valve members 184, 186 each include an access valve 190 to control the flow of gas from a cylinder 10', 10" into the adaptor 182. In the examples illustrated in FIGS. 15-19, the first valve member 184 is engageable to the primary cylinder 10' and the second valve member 186 is engageable to the reserve cylinder 10". The reservoir changing device 180 additionally includes a motor and transmission subassembly 192 to operate the access valves 190, a power supply 194 to provide power to the motor and transmission subassembly 192; and a control subassembly 196. The control subassembly 196 includes a receiver (not shown) and a motor switch mechanism (not shown), the receiver being capable of receiving an alarm indication and actuating the motor switch mechanism to activate the motor and transmission subassembly 192. The reservoir changing device 180 optionally includes a first adaptor arm 198 and a second adaptor arm 200 to increase the distance between the adaptor 182 and the cylinders 10', 10". The first adaptor arm 198 is in gas-tight engagement with both the adaptor 182 and the first valve member 184, and the second adaptor arm 200 is in gas-tight engagement with the adaptor 182 and the second valve member 186.

Figure 15A:
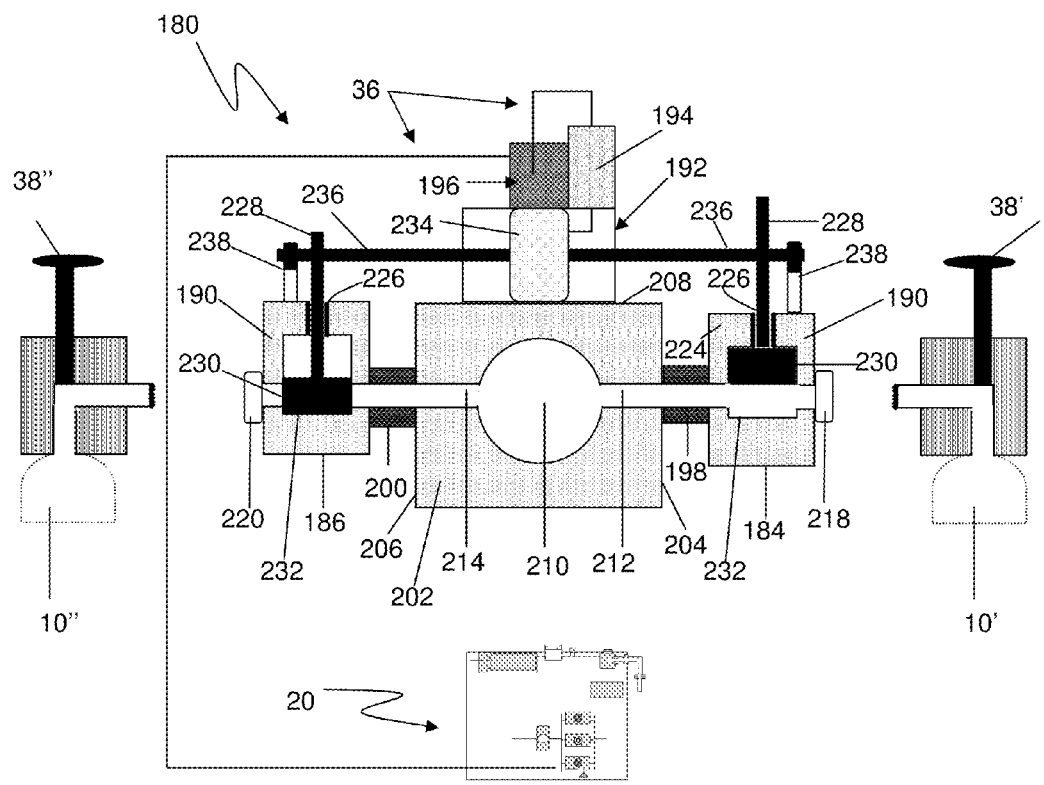
FIG. 15A shows a frontal semi schematic cross section, taken through the center of the adaptor, of an embodiment of the reservoir changing device of the present invention.
Figure 15B:
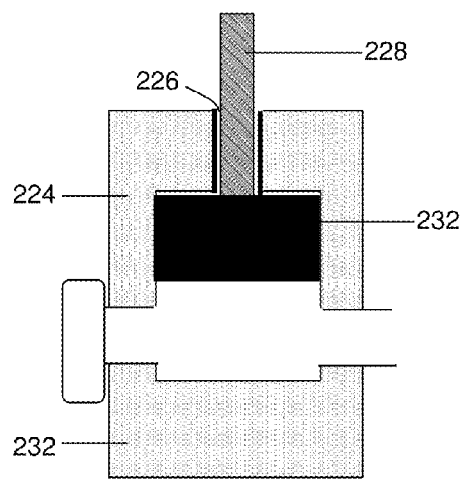
FIG. 15B shows a frontal semi-schematic cross section of a valve member.
Figure 16:
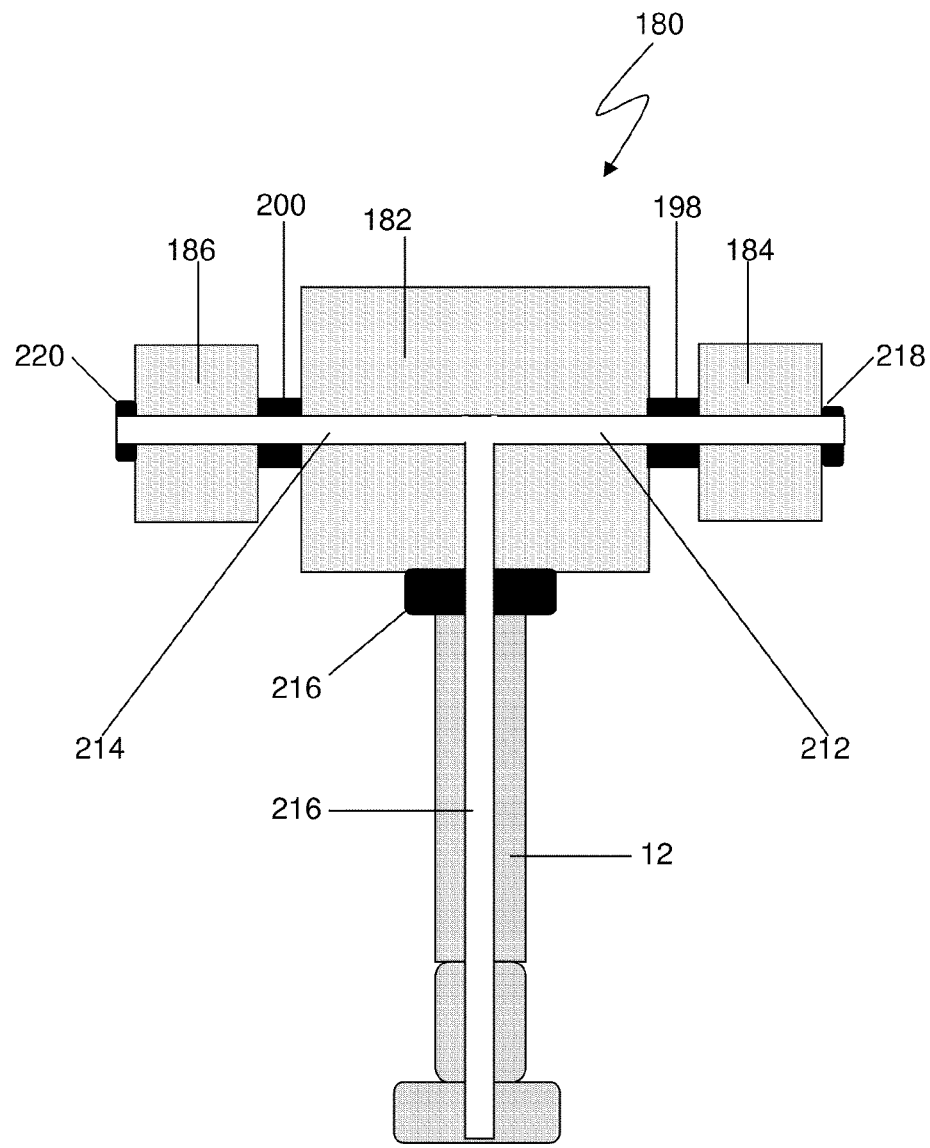
FIG. 16. shows a longitudinal section of the reservoir changing device and an attached regulator.
Figure 17:
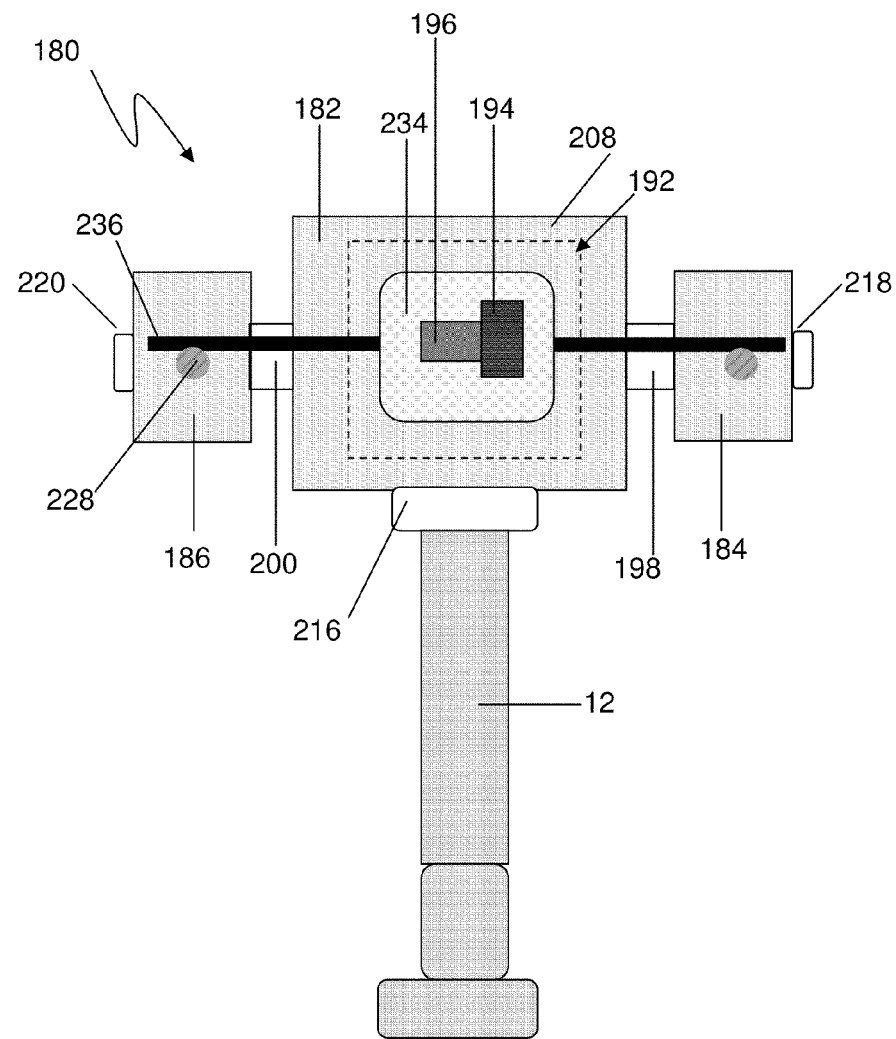
FIG. 17 shows a top elevation of the reservoir changing device and an attached regulator.
Figure 18:
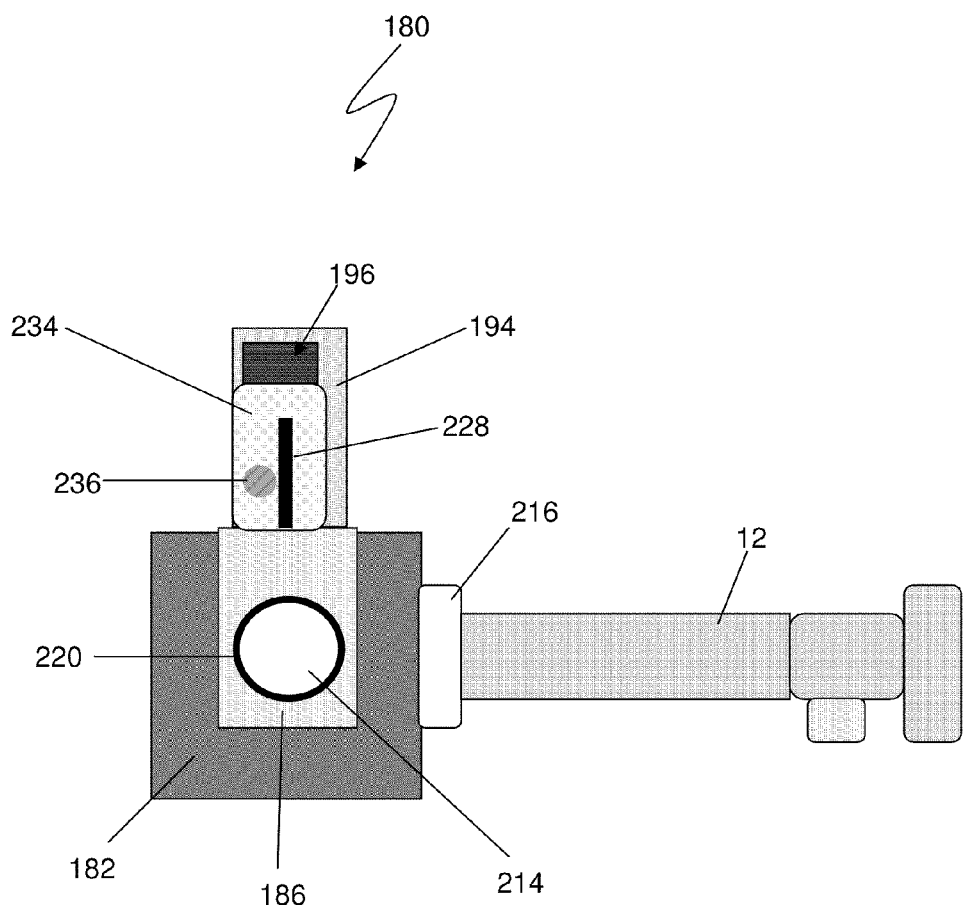
FIG. 18. shows a side elevation of the reservoir changing device and an attached regulator, as viewed from a reserve gas cylinder.
Figure 19:
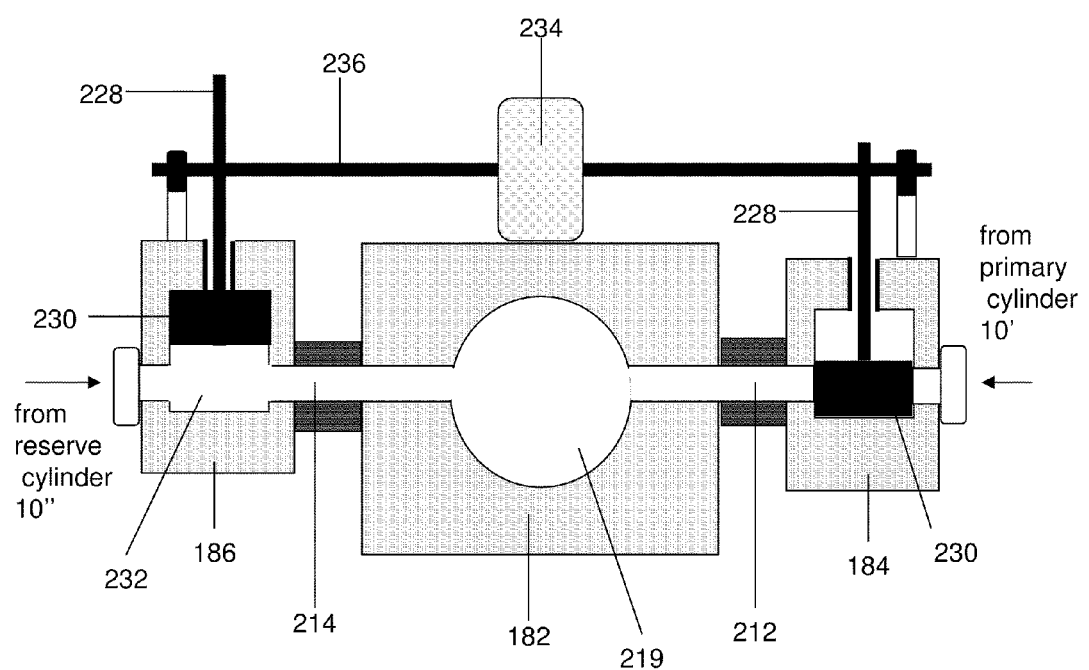
FIG. 19 shows a frontal semi schematic cross section of the access valves of the reservoir changing device, positioned to close a primary gas cylinder and open a reserve gas cylinder to a pressurized gas system.

The adaptor 182 is preferably a rectangular solid having at least a front surface 202, a first side surface 204 opposite a second side surface 206 and a top surface 208. The adaptor 182 defines three intersecting channels extending therethrough, the channels preferably intersecting at a T shaped junction, as best shown in FIG. 16, although Y-shaped junctions and other junction forms can also be included. The channels include a regulator channel 210, a first valve channel 212, and a second valve channel 214. The regulator channel 210 can originate from any point within the adaptor 182, preferably from the center of the adaptor 182, and extends through the front surface 202 to terminate in a regulator port 216, the regulator port 216 being engageable to a gas regulator 12. The first valve channel 212 originates at the regulator channel 210, extends through the first side surface 204 of the adapter 182, and through the first valve member 184, to terminate in a primary reservoir port 218 adapted to engage a primary cylinder 10', or other primary reservoir, in gas-tight engagement. If a first adaptor arm 198 is included, then the first valve channel 212 additionally extends through the first adaptor arm 198. The second valve channel 214 originates at the regulator channel 210 and extends in a direction opposite that of the first valve channel 212, through the second side surface 206 of the adaptor 182, through the second valve member 186, to terminate in a reserve reservoir port 220 adapted to engage a reserve cylinder 10" in gas-tight engagement. The second adaptor arm 200 can also be included in this path, as illustrated in FIGS. 15 and 17. The first and second adaptor arms 198, 200 permit a cylinder 10', 10" or other reservoirs to be situated a distance away from the reservoir changing device 180 and regulator 12, the distance being determined by the length of the adaptor arms 198, 200. The primary and reserve reservoir ports 218, 220 can include any adapters known in the art to achieve gas-tight engagement to a particular type of reservoir.

The first and second valve members 184, 186 each include an access valve 190 including a bonnet 224 defining a threaded central bore 226 therethrough, a correspondingly threaded valve stem 228 extending through the central bore 226 and threadingly engaged therewith. The valve stem 228 has an upper end extending through the bonnet 224 and a lower end including a valve body 230. The access valve 190 also includes a valve seat 232, which is continuous with one of the valve channels 212 or 214, and which is complementary in shape to the valve body 230, to sealingly engage the valve body 230 thereby occluding the valve channel 212 or 214 to block the flow of gas from the primary or reserve cylinder 10', 10".

The motor and transmission subassembly 192 is preferably situated on the top surface 208 of the adaptor 182. The motor and transmission subassembly 192 includes at least one rotary motor 234, preferably electrically powered, the motor having a motor shaft (not shown) operatively connected to at least one worm gear 236. If the reservoir changing device 180 is intended only to open a reserve cylinder 10" or other reserve reservoir, then only a single worm gear 236 is included, the worm gear 236 extending laterally along the top surface of the adaptor 182, in a direction paralleling the second valve channel 214 to operatively engage the threads of the valve stem 228 of the second valve member 186. Activation of the motor 234 causes the worm gear 236 to rotate to confer counterclockwise motion to the valve stem 228. This causes the valve stem 228 to rise through the central bore 226 of the bonnet 224, lifting the valve body 230 from the valve seat 232, and thereby allowing gas from the reserve cylinder 10" to flow through the second valve channel 214, into the adaptor 182, and hence into the gas regulator 12.

If the reservoir changing device 180 is intended both to open a reserve cylinder 10" and to close a depleted primary cylinder 10', then the device 180 includes two worm gears 236, with a first worm gear 236 engaging the valve stem 228 of the first valve member 184 and a second worm gear 236 engaging the valve stem 228 of the second valve member 186. Preferably both worm gears 236 are operatively connected to a single motor 234, the worm gears 236 being threaded in complementary directions, with a first worm gear 236 lifting the valve stem 228 of the second valve member 186 to allow gas from the reserve cylinder 10" to flow into the adaptor 182, and the second worm gear 236 simultaneously lowering the valve stem 228 of the first valve member 184, to close the primary cylinder 10' off from the adaptor 182. It is desirable to close the depleted primary cylinder 10' in order to prevent gas from the reserve cylinder 10" from being wastefully diverted into the depleted primary cylinder 10'.

The device 180 can include at least one worm gear stabilizer, for example worm gear guide 238, to stabilize the worm gear 236 during its rotation. The worm gear guide 238 includes a bracket extending from a valve bonnet 224 to pivotingly engage the worm gear 236.

Preferably, a clutch (not shown) or other means to disengage the motor 234 from the worm gear 236 is additionally included in the power and transmission subassembly 192. Disengagement of the worm gear 236 from the motor 234 permits a user to manually open or close an access valve 190 in order to prepare the device 180 for use. To further facilitate manual operation of an access valve, the valve stem 228 can additionally include a handle (not shown) for manual rotation of a valve stem 228 within the central bore 226 of a bonnet 234.

The materials employed in the reservoir changing device 180 are selected according to the nature of the gas in the pressurized gas system, and to the level of pressure to which it will be exposed. In general, any materials suitable for the reservoir itself, and for its valves and fittings, will also be suitable for use in the device 180.

The motor 234 can include motors of any type, size, speed, power output, and power source appropriate to the size and weight of the access valves 190. It is preferable to include a motor 234 with sufficiently high initial torque to overcome the inertia of the valve stem 228, and with relatively low speed and high torque, as power to firmly seat the valve body 230 is more important than speed of movement. It is also preferable to provide the motor 234 with a shut-off mechanism (not shown) to deactivate the motor 234 when the valve body 230 has reached the end of its travel. Travel limit sensors and torque limit sensors that will cut off power to the motor are well known in the art.

The reservoir changing device 180 can alternatively include any motive force and any valve operation means that will appropriately open and close access valves 190. For example, an individual motor 234 can be operatively connected directly to each valve stem, to supply torque directly to the valve stem. (not shown). Valves can alternatively be opened and closed by means of springs (not shown) actuated by the control subassembly 196. Spring powered valves are feasible for low pressure reservoirs such as portable liquid propane tanks.

The power supply 194 is selected according to the characteristics of the motor. Preferably the power supply 194 includes a battery with sufficient power and capacity to meet the demands of the selected motor 234. Battery power insulates the reservoir changing device 180 from interruptions in house current, and permits use of the device 180 in the field. For greater demands, alternative power sources include, but are not limited to, DC and AC house current.

The control subassembly 196 can be situated in any location from which it can actuate the motor 234. The control subassembly includes a master on-off switch (not shown) to permit a user to activate and deactivate the reservoir changing device 180, and a motor switch (not shown) to activate and deactivate the motor 234. The control subassembly 196 additionally includes a receiver (not shown) to receive an alarm indication that the gas pressure in the primary cylinder 10' has diminished to a predetermined level. The receiver can be any device capable of receiving wired or wireless broadcast alarm indications and actuating a motor switch to activate the motor 234. Receivers can include, but are not limited to, a radio receiver; a wired or cellular phone receiver, a pager, a receiving device on a wired or wireless LAN, a Bluetooth™ equipped device, and a wired intercom substation. The control subassembly 196 optionally includes a manual operation switch (not shown) to permit a user to manually activate the motor 234 in order to move the valves into desired positions. In the example illustrated in FIG. 15, the control subassembly 196 is operatively connected to the alarm device 20, and to the motor 234, by connection means 36 such as wiring, printed circuits, and the like.

In operation, the initial condition of the reservoir changing device is as illustrated in FIG. 15, with the access valve 190 of the first valve member 184 in raised, open position, and the access valve of the second valve member 186 in closed position. A user engages a regulator 12 to the regulator port 216. The user engages a primary cylinder 10' or other primary reservoir with the primary reservoir port 218, and a reserve cylinder 10" to the reserve reservoir port 220. The user opens the main valve 38' of the primary cylinder 10' and the main valve 38" of the reserve cylinder 10". A stream of pressurized gas flows from the primary cylinder 10', through the first valve channel 212 and the regulator channel 210, and into the regulator 12. The user operates the master power switch (not shown) to activate the reservoir changing device 180. The user activates the alarm device 20 or any other alarm indicator operatively connected to the reservoir changing device 180. When pressure in the primary cylinder 10' reaches a predetermined level, an alarm indication is received by the receiver (not shown) of the control subassembly 196. The receiver actuates the motor switch (not shown) to activate the motor 234 to rotate the worm gears 236, thereby opening the access valve 190 of the second valve member 186 and closing the access valve 190 of the first valve member 184, to achieve the final state illustrated in FIG. 19. In the final state, the stream of pressurized gas flows from the reserve cylinder 10", through the second valve channel 214 and the regulator channel 210 and into the regulator 12. The primary cylinder 10' is closed off from the pressurized gas system.

An advantage of the reservoir changing device 180 is that it can be made in any size, and combined with any fittings, to be applicable to any combination of reservoirs and regulator. Another advantage is that the reservoirs need not be closely adjacent to the regulator 12, as the first and second adaptor arms 198, 200 can be extended to any desired length. This allows flexibility in reservoir arrangement. The reservoir changing device 180 can also be readily adapted to accept and control more than one reserve reservoir by the inclusion of additional valve members.

The present invention is readily adapted for use as an alarm device for pressurized systems for gases other than oxygen through simple substitutions of materials, such as gas-tight seals, and of valves and sensors appropriate for the particular gas, as will be well known to this skilled in the art of that gas. Through such substitutions, the present invention is a useful alarm device for pressurized systems containing for example propane, medical air, carbon dioxide, hydrogen, nitrogen, helium, argon, ethylene, xenon, and mixtures thereof. The present invention is readily adapted to any type of gas regulator, including two-stage gas regulators. The present invention is similarly readily adapted for use as an alarm device 20 for systems containing pressurized liquids and pressurized flowable solids.

While illustrative embodiments of the invention have been disclosed herein, it is understood that other embodiments and modifications may be apparent to those of ordinary skill in the art.

The invention claimed is:

1. A gas flow warning alarm device comprising:
   a flow sensing and error signal generator including:
   a gas flow sensor for sensing a gas flow rate and an error signal generating subassembly operatively connected to said gas flow sensor, said gas flow sensor configured to actuate said error signal generator upon detecting a gas flow rate violating said at least one predetermined gas flow rate limit, said error signal generating subassembly generating an error signal in response to actuation by said gas flow sensor;
   said gas flow sensor including a gas flow inlet to direct a column of pressurized gas from an upstream path into said gas flow sensor;
   said upstream path being constantly open to a main valve of a pressurized gas reservoir;
   said gas flow sensor including a gas flow outlet to direct said column of pressurized gas out of said gas flow sensor to a downstream path;
   said downstream path being constantly open to an end use appliance;
   an indicator subassembly including at least one indicator mechanism operatively connected to said error signal generating subassembly, said at least one indicator mechanism being activatable by said error signal to produce a perceptible alarm indication;
   at least one power subassembly including at least one power source operatively connected to a master power switch for powering said flow sensor, said error signal generating subassembly and said indicator subassembly, and activating and deactivating said gas flow warning alarm device;

at least one housing to contain at least said gas flow sensor and said at least one power subassembly; and connection means for operatively interconnecting said gas flow sensor and error signaling subassembly, said indicator subassembly, and said power subassembly;

said gas flow warning alarm device further including a reservoir pressure sensing and pressure error signal generating subassembly to produce an alarm indication when the gas pressure in a pressurized gas reservoir violates said at least one predetermined limit including said reservoir pressure sensor to sense the gas pressure of a pressurized gas reservoir, and a pressure error signal generator operatively connected to said reservoir pressure sensor, said reservoir pressure sensor being configured to actuate said pressure error signal generator upon detecting a reservoir gas pressure outside of the predetermined limit, said pressure error signal generator being configured to generate an error signal in response to actuation by said reservoir pressure sensor;

wherein said pressure error signal generator is operatively connected to said indicator subassembly; and wherein said pressure error signal generator activates said at least one indicator mechanism to produce at least one alarm indication that is distinguishable from said alarm indication produced by an alarm mechanism activated by said gas flow error signal generator.

2. The gas flow warning alarm device according to claim 1 wherein said gas flow rate is further defined as a flow rate of gases selected from the group including oxygen flow rate, compressed air, carbon dioxide, hydrogen, nitrogen, helium, argon, ethylene, xenon, and mixtures thereof.

3. The gas flow warning alarm device according to claim 1 further including a tubular gas flow inlet conduit having a first end and an opposite second end and having an upstream orifice at said first end and a downstream orifice at said second end, said upstream orifice of said gas flow inlet conduit being in gas-tight engagement with a pressurized gas system at any point upstream of said end use appliance, said downstream orifice of said gas inlet being in gas-tight engagement with said gas flow inlet of said gas flow sensor, to direct said column of pressurized gas into said gas flow inlet of said gas flow sensor.

4. The gas flow warning alarm device according to claim 1 further including a tubular gas flow outlet conduit having a first end and an opposite second end and having an upstream orifice at said first end and a downstream orifice at said second end, said upstream orifice of said gas flow outlet conduit being in gas-tight engagement with said gas flow outlet of said gas flow sensor, said downstream orifice of said gas flow outlet conduit being in gas-tight engagement with said pressurized gas system at any point downstream of said upstream orifice of a gas flow inlet conduit and upstream of said end use appliance, to direct said column of pressurized gas out of said gas flow outlet of said gas flow sensor.

5. The gas flow warning alarm device according to claim 1 wherein said gas flow sensor and said error signal generator are incorporated into a gas flow switch.

6. The gas flow warning alarm device according to claim 1 wherein said at least one predetermined gas flow rate limit is a minimum gas flow rate.

7. The gas flow warning alarm device according to claim 1 wherein said at least one predetermined gas flow rate limit is a maximum gas flow rate.

8. The gas flow warning alarm device according to claim 1 wherein said at least one predetermined gas flow rate limit is a either a minimum gas flow rate or a maximum gas flow rate.

9. The gas flow warning alarm device according to claim 1 wherein said gas flow sensor is a gas flow sensor of a type selected from the group including a paddle type sensor, a propeller type sensor, a vane type sensor, a shuttle type sensor, a mass flow type sensor, a reed switch sensor, a calorimetric sensor, and a Bernouli type sensor.

10. The gas flow warning alarm device according to claim 1 wherein said gas flow sensor is capable of quantitative measurement of a gas flow rate.

11. The gas flow warning alarm device according to claim 1 wherein said at least one indicator mechanism is an audio device selected from the group including a bell, a mechanical buzzer, and electronic tone synthesizer.

12. The gas flow warning alarm device according to claim 1 wherein said at least one indicator mechanism is a visual display device selected from the group including an incandescent lamp, a fluorescent tube, a light emitting diode, a liquid crystal display, and a strobe lamp.

13. The gas flow warning alarm device according to claim 1 wherein said at least one indicator mechanism is a broadcast signal transmitter to communicate an alarm signal to at least one remote receiver, thereby eliciting a final alarm indication in said remote receiver, said broadcast signal transmitter being selected from the group including a radio transmitter, a telephone transmitter; a wireless local area network (LAN) router, an Ethernet® router, a Bluetooth™ transmitter, an intercom base station, and a signal generator to control a remotely controlled reservoir-changing device.

14. The gas flow warning alarm device according to claim 1 wherein said indicator subassembly further includes a silencing switch to deactivate at least one of said activated indicator mechanisms.

15. The gas flow warning alarm device according to claim 14 wherein the actuation of said silencing switch interrupts a connection between said at least one power subassembly and said at least one indicating mechanism.

16. The gas flow warning alarm device according to claim 14 wherein said silencing switch further includes a security lock and key to restrict the activation of said silencing switch.

17. The gas flow warning alarm device according to claim 1 wherein said indicator subassembly additionally includes at least one microcontroller operatively connected to said flow sensing and error signaling subassembly, and to at least one of said indicator mechanisms, said microcontroller being programmed with at least one routine activatable by said error signal, the at least one routine commanding said at least one indicator mechanism to produce an alarm indication.

18. The gas flow warning alarm device according to claim 17 wherein said at least one routine includes at least one routine to command an audio device to produce an audible alarm tone.

19. The gas flow warning alarm device according to claim 17 wherein said at least one routine includes at least one routine to command a visual display device to produce a visual alarm display.

20. The gas flow warning alarm device according to claim 17 wherein said at least one routine includes at least one routine to command a broadcast signal transmitter to transmit an alarm message to a remote receiver.

21. The gas flow warning alarm device according to claim 17 wherein said gas flow sensor is capable of quantitative measurement of a gas flow rate, and said at least one routine includes at least one routine to command a digital display to display a gas flow rate.

22. The gas flow warning alarm device according to claim 17 wherein the actuation of a silencing switch inhibits said at least one routine from commanding said at least one indicator mechanism to produce an alarm indication.

23. The gas flow warning alarm device according to claim 1 wherein said at least one housing is positioned in a situation selected from the group of situations including mounted upon a regulator, depending from a regulator outlet, mounted upon a cylinder, mounted upon a flow meter, mounted upon a humidifier, mounted upon the cart of a portable oxygen cylinder, resting on a surface, and incorporated into a regulator.

24. The gas flow warning alarm device according to claim 1 wherein said at least one housing includes a primary housing to contain at least said gas flow sensor and said at least one power subassembly, and at least one remote housing to contain at least said indicator subassembly and said at least one power subassembly.

25. The gas flow warning alarm device according to claim 1 wherein said gas flow inlet is in gas-tight engagement with an oxygen concentrator.

26. The gas flow warning alarm device according to claim 1 wherein said pressure error signal generator is operatively connected to a gas pressure indicator subassembly.

27. The gas flow warning alarm device according to claim 26 wherein said pressure error signal generator activates at least one indicator mechanism to produce at least one alarm indication that is distinguishable from the alarm indications produced by said alarm mechanism activated by said gas flow error signal generator.

28. The gas flow warning alarm device according to claim 27 wherein said at least one indicator mechanism includes a signal generator to control a remotely controlled reservoir-changing device.

29. The gas flow warning alarm device according to claim 1 wherein said at least one indicator mechanism includes a signal generator to control a remotely controlled reservoir-changing device.

30. The gas flow warning alarm device according to claim 1 wherein said reservoir pressure sensor is in gas-tight engagement with said pressurized gas system by means of a tubular pressure conduit.

31. The gas flow warning alarm device according to claim 1 wherein said reservoir pressure sensor is in gas-tight engagement with said pressurized gas system at any point downstream of said main valve of said pressurized gas reservoir and upstream of said pressure valve.

32. The gas flow warning alarm device according to claim 1 wherein said reservoir pressure sensor and said pressure error signal generator are incorporated into a gas pressure switch.

33. The gas flow warning alarm device according to claim 1 wherein said at least one housing includes a primary housing to contain at least said reservoir pressure sensing and pressure error signal generating subassembly, and said at least one power subassembly, and at least one remote housing including at least an indicator subassembly, and said at least one power subassembly.

34. The gas flow warning alarm device according to claim 1 wherein said pressurized gas reservoir is a reservoir containing oxygen.

35. The gas flow warning alarm device according to claim 1 additionally including a downstream accessory device, said accessory device having at least an inlet port in gas-tight engagement with a pressurized gas system at any point downstream of said gas flow sensor, said downstream accessory device being selected from the group including said humidifier, a filter, said flow meter, and an oxygen analyzer.

36. The gas flow warning alarm device according to claim 1 additionally including an oxygen sensor in gas-tight engagement with said pressurized gas system, said oxygen sensor being operatively connected to a voltmeter, said voltmeter being configured to measure the voltage generated by said oxygen sensor, calculate from said voltage a corresponding value of the percentage of oxygen in a pressurized gas system, and display said value.

37. The gas flow warning device of claim 36 wherein said voltmeter is operatively connected to an $O^2\%$ alarm indicator, said voltmeter being additionally configured to transmit an error signal to said $O^2\%$ alarm indicator upon calculating a percent oxygen value below a predetermined limit.

38. The gas flow warning alarm device according to claim 1 additionally including an upstream accessory device, said accessory device having at least an inlet port in gas-tight engagement with a pressurized gas system at any point upstream of said gas flow sensor, said upstream accessory device being selected from the group including said humidifier and said flow meter.

39. A method for detecting gas flow and reservoir pressure malfunctions in a pressurized gas system, said method including the steps of:
    engaging a gas flow inlet of a flow sensor to a column of pressurized gas from an upstream path,
    maintaining the upstream path constantly open to a main valve of a pressurized gas reservoir;
    engaging a gas flow outlet of the flow sensor to direct a column of pressurized gas out of the flow sensor and into a downstream path ending in an end use appliance;
    maintaining the downstream path constantly open to the end use appliance;
    engaging a gas pressure inlet of a gas pressure sensor downstream of the pressurized gas reservoir and upstream of a flow valve of a gas regulator;
    sensing a gas flow rate violating at least one predetermined limit;
    actuating a gas flow error signal generator upon sensing the gas flow rate violating the at least one predetermined limit;
    generating a gas flow error signal in response to the activating of the gas flow error signal generator;
    activating at least one indicator mechanism by means of the gas flow error signal;
    producing a perceptible gas flow alarm indication by means of the indicator mechanism;
    sensing a gas pressure of the pressurized gas reservoir violating at least one predetermined limit;
    actuating a gas pressure error signal generator upon sensing the gas pressure of the pressurized gas reservoir violating the at least one predetermined limit;
    generating a gas pressure error signal in response to the actuating of the gas pressure signal generator;
    activating the at least one indicator mechanism by means of the gas pressure error signal; and
    producing a perceptible gas pressure alarm indication by means of the at least one indicator mechanism, the gas pressure alarm indication being distinguishable from the alarm indication produced by an alarm mechanism activated by the gas flow error signal generator.

40. A gas flow warning alarm device comprising:
    a flow sensing and error signal generator including:
    a gas flow sensor for sensing a gas flow rate and an error signal generating subassembly operatively connected to said gas flow sensor, said gas flow sensor configured to actuate said error signal generator upon detecting a gas flow rate violating said at least one predetermined gas flow rate limit, said error signal generating subassembly generating an error signal in response to actuation by said gas flow sensor;

said gas flow sensor including a gas flow inlet to direct a column of pressurized gas from an upstream path into said gas flow sensor;

said upstream path being constantly open to a main valve of a pressurized gas reservoir;

said gas flow sensor including a gas flow outlet to direct said column of pressurized gas out of said gas flow sensor to a downstream path;

said downstream path being constantly open to an end use appliance;

an indicator subassembly including at least one indicator mechanism operatively connected to said error signal generating subassembly, said at least one indicator mechanism being activatable by said error signal to produce a perceptible alarm indication;

at least one power subassembly including at least one power source operatively connected to a master power switch for powering said flow sensor, said error signal generating subassembly and said indicator subassembly, and activating and deactivating said gas flow warning alarm device;

at least one housing to contain at least said gas flow sensor and said at least one power subassembly; and connection means for operatively interconnecting said gas flow sensor and error signaling subassembly, said indicator subassembly, and said power subassembly, said gas flow warning alarm device further including a reservoir pressure sensing and pressure error signal generating subassembly to produce an alarm indication when the gas pressure in a pressurized gas reservoir violates said at least one predetermined limit including a reservoir pressure sensor to sense the gas pressure of said pressurized gas reservoir, and a pressure error signal generator operatively connected to said reservoir pressure sensor, said reservoir pressure sensor being configured to actuate said pressure error signal generator upon detecting a reservoir gas pressure outside of the predetermined limit, said pressure error signal generator being configured to generate an error signal in response to actuation by said reservoir pressure sensor;

wherein said pressure error signal generator is operatively connected to a gas pressure indicator subassembly; and wherein said pressure error signal generator activates at least one indicator mechanism to produce at least one alarm indication that is distinguishable from said alarm indications produced by an alarm mechanism activated by said gas flow error signal generator.

41. A gas flow warning alarm device comprising:
a flow sensing and error signal generator including:
a gas flow sensor for sensing a gas flow rate and an error signal generating subassembly operatively connected to said gas flow sensor, said gas flow sensor configured to actuate said error signal generator upon detecting a gas flow rate violating said at least one predetermined gas flow rate limit, said error signal generating subassembly generating an error signal in response to actuation by said gas flow sensor;

said gas flow sensor including a gas flow inlet to direct a column of pressurized gas from an upstream path into said gas flow sensor;

said gas flow inlet upstream path being constantly open to a main valve of a pressurized gas reservoir;

said gas flow sensor including a gas flow outlet to direct said column of pressurized gas out of said gas flow sensor to a downstream path;

said downstream path being constantly open to an end use appliance;

an indicator subassembly including at least one indicator mechanism operatively connected to said error signal generating subassembly, said at least one indicator mechanism being activatable by said error signal to produce a perceptible alarm indication;

at least one power subassembly including at least one power source operatively connected to a master power switch for powering said flow sensor, said error signal generating subassembly and said indicator subassembly, and activating and deactivating said gas flow warning alarm device;

at least one housing to contain at least said gas flow sensor and said at least one power subassembly; and connection means for operatively interconnecting said gas flow sensor and error signaling subassembly, said indicator subassembly, and said power subassembly, said gas flow warning alarm device further including a reservoir pressure sensing and pressure error signal generating subassembly to produce an alarm indication when the gas pressure in a pressurized gas reservoir violates said at least one predetermined limit including a reservoir pressure sensor to sense the gas pressure of said pressurized gas reservoir, and a pressure error signal generator operatively connected to said reservoir pressure sensor, said reservoir pressure sensor being configured to actuate said pressure error signal generator upon detecting a reservoir gas pressure outside of the predetermined limit, said pressure error signal generator being configured to generate an error signal in response to actuation by said reservoir pressure sensor;

wherein said at least one indicator mechanism operatively connected to said indicator subassembly includes a signal generator to control a remotely controlled reservoir-changing device.

42. A gas flow warning alarm device comprising:
a flow sensing and error signal generator including:
a gas flow sensor for sensing a gas flow rate and an error signal generating subassembly operatively connected to said gas flow sensor, said gas flow sensor configured to actuate said error signal generator upon detecting a gas flow rate violating said at least one predetermined gas flow rate limit, said error signal generating subassembly generating an error signal in response to actuation by said gas flow sensor;

said gas flow sensor including a gas flow inlet to direct a column of pressurized gas from an upstream path into said gas flow sensor;

said gas flow inlet upstream path being constantly open to a main valve of a pressurized gas reservoir;

said gas flow sensor including a gas flow outlet to direct said column of pressurized gas out of said gas flow sensor to a downstream path;

said downstream path being constantly open to an end use appliance;

an indicator subassembly including at least one indicator mechanism operatively connected to said error signal generating subassembly, said at least one indicator mechanism being activatable by said error signal to produce a perceptible alarm indication;

at least one power subassembly including at least one power source operatively connected to a master power switch for powering said flow sensor, said error signal generating subassembly and said indicator subassembly, and activating and deactivating said gas flow warning alarm device;

at least one housing to contain at least said gas flow sensor and said at least one power subassembly; and connection means for operatively interconnecting said gas flow sensor and error signaling subassembly, said indicator subassembly, and said power subassembly;

said gas flow warning alarm device further including a reservoir pressure sensing and pressure error signal generating subassembly to produce an alarm indication when the gas pressure in a pressurized gas reservoir violates said at least one predetermined limit including said reservoir pressure sensor to sense the gas pressure of a pressurized gas reservoir, and a pressure error signal generator operatively connected to said reservoir pressure sensor, said reservoir pressure sensor being configured to actuate said pressure error signal generator upon detecting a reservoir gas pressure outside of the predetermined limit, said pressure error signal generator being configured to generate an error signal in response to actuation by said reservoir pressure sensor;

wherein said at least one indicator mechanism is a broadcast signal transmitter to communicate an alarm signal to at least one remote receiver, thereby eliciting a final alarm indication in said remote receiver, said broadcast signal transmitter being selected from the group including a radio transmitter, a telephone transmitter; a wireless local area network (LAN) router, an Ethernet® router, a Bluetooth™ transmitter, an intercom base station, and a signal generator to control a remotely controlled reservoir-changing device.

43. A gas flow warning alarm device comprising:

a flow sensing and error signal generator including:

a gas flow sensor for sensing a gas flow rate and an error signal generating subassembly operatively connected to said gas flow sensor, said gas flow sensor configured to actuate said error signal generator upon detecting a gas flow rate violating said at least one predetermined gas flow rate limit, said error signal generating subassembly generating an error signal in response to actuation by said gas flow sensor;

said gas flow sensor including a gas flow inlet to direct a column of pressurized gas from an upstream path into said gas flow sensor;

said gas flow inlet upstream path being constantly open to a main valve of a pressurized gas reservoir;

said gas flow sensor including a gas flow outlet to direct said column of pressurized gas out of said gas flow sensor to a downstream path;

said downstream path being constantly open to an end use appliance;

an indicator subassembly including at least one indicator mechanism operatively connected to said error signal generating subassembly, said at least one indicator mechanism being activatable by said error signal to produce a perceptible alarm indication;

at least one power subassembly including at least one power source operatively connected to a master power switch for powering said flow sensor, said error signal generating subassembly and said indicator subassembly, and activating and deactivating said gas flow warning alarm device;

at least one housing to contain at least said gas flow sensor and said at least one power subassembly; and connection means for operatively interconnecting said gas flow sensor and error signaling subassembly, said indicator subassembly, and said power subassembly, said gas flow warning alarm device further including a reservoir pressure sensing and pressure error signal generating subassembly to produce an alarm indication when the gas pressure in a pressurized gas reservoir violates said at least one predetermined limit including said reservoir pressure sensor to sense the gas pressure of a pressurized gas reservoir, and a pressure error signal generator operatively connected to said reservoir pressure sensor, said reservoir pressure sensor being configured to actuate said pressure error signal generator upon detecting a reservoir gas pressure outside of the predetermined limit, said pressure error signal generator being configured to generate an error signal in response to actuation by said reservoir pressure sensor;

wherein said indicator subassembly further includes a silencing switch to deactivate at least one of said activated indicator mechanisms, said silencing switch including a security lock and key to restrict the activation of said silencing switch.

* * * * *